(12) United States Patent
Puri et al.

(10) Patent No.: US 8,546,409 B2
(45) Date of Patent: Oct. 1, 2013

(54) METHODS OF TREATMENT FOR SOLID TUMORS

(75) Inventors: Kamal D. Puri, Lynnwood, WA (US); Jerry B. Evarts, Foster City, CA (US); Brian Lannutti, Seattle, WA (US); Neill Giese, Seattle, WA (US)

(73) Assignee: Gilead Calistoga LLC, Foster City, CA (US)

( * ) Notice: Subject to any disclaimer, the term of this patent is extended or adjusted under 35 U.S.C. 154(b) by 394 days.

(21) Appl. No.: 12/763,991

(22) Filed: Apr. 20, 2010

(65) Prior Publication Data
US 2011/0044942 A1 Feb. 24, 2011

Related U.S. Application Data

(60) Provisional application No. 61/171,047, filed on Apr. 20, 2009.

(51) Int. Cl.
*A61K 31/517* (2006.01)

(52) U.S. Cl.
USPC ........................................................ 514/266.1

(58) Field of Classification Search
None
See application file for complete search history.

(56) References Cited

U.S. PATENT DOCUMENTS

| | | | |
|---|---|---|---|
| 3,322,756 A | 5/1967 | Ruschig et al. |
| 3,691,016 A | 9/1972 | Patel |
| 3,897,432 A | 7/1975 | Shen et al. |
| 3,969,287 A | 7/1976 | Jaworek et al. |
| 3,984,555 A | 10/1976 | Amschler et al. |
| 4,179,337 A | 12/1979 | Davis et al. |
| 4,183,931 A | 1/1980 | Wolfe et al. |
| 4,195,128 A | 3/1980 | Hildebrand et al. |
| 4,225,489 A | 9/1980 | Rolf et al. |
| 4,229,537 A | 10/1980 | Hodgins et al. |
| 4,247,642 A | 1/1981 | Hirohara et al. |
| 4,289,872 A | 9/1981 | Denkewalter et al. |
| 4,301,144 A | 11/1981 | Iwashita et al. |
| 4,330,440 A | 5/1982 | Ayers et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,925,673 A | 5/1990 | Steiner et al. |
| 5,013,556 A | 5/1991 | Woodle et al. |
| 5,225,347 A | 7/1993 | Goldberg et al. |
| 5,229,490 A | 7/1993 | Tam |
| 5,378,725 A | 1/1995 | Bonjouklian et al. |
| 5,480,906 A | 1/1996 | Creemer et al. |
| RE35,862 E | 7/1998 | Steiner et al. |
| 5,858,753 A | 1/1999 | Chantry et al. |
| 5,882,910 A | 3/1999 | Chantry et al. |
| 5,948,664 A | 9/1999 | Williams et al. |
| 5,985,589 A | 11/1999 | Chantry et al. |
| 6,046,049 A | 4/2000 | Monia et al. |
| 6,048,970 A | 4/2000 | Lal et al. |
| 6,277,981 B1 | 8/2001 | Tu et al. |
| 6,291,220 B1 | 9/2001 | Williams et al. |
| 6,369,038 B1 | 4/2002 | Blumenfeld et al. |
| 6,410,224 B1 | 6/2002 | Stinchcomb et al. |
| 6,426,337 B1 | 7/2002 | Cox et al. |
| 6,482,623 B1 | 11/2002 | Vanhaesebroeck et al. |
| 6,518,277 B1 | 2/2003 | Sadhu et al. |
| 6,667,300 B2 | 12/2003 | Sadhu et al. |
| 6,696,250 B1 | 2/2004 | Cech et al. |
| 6,800,620 B2 | 10/2004 | Sadhu et al. |
| 6,949,535 B2 | 9/2005 | Sadhu et al. |
| 7,932,260 B2 | 4/2011 | Fowler et al. |
| 8,138,195 B2 | 3/2012 | Sadhu et al. |
| 8,207,153 B2 | 6/2012 | Fowler et al. |
| 2004/0023390 A1 | 2/2004 | Davidson et al. |
| 2004/0092561 A1 | 5/2004 | Ruckle et al. |
| 2004/0121996 A1 | 6/2004 | Barvian et al. |

(Continued)

FOREIGN PATENT DOCUMENTS

| EP | 0 525 960 A1 | 2/1993 |
|---|---|---|
| EP | 0 525 960 B1 | 2/1993 |

(Continued)

OTHER PUBLICATIONS

Berge et al., J. Pharm. Sci. (1977) 66:1.
Chantry et al., J. Biol. Chem. (1997) 272:19236-19241.
Denley et al., Oncogene (2008) 27(18):2561-2574.
International Search Report for PCT/US2010/031794, mailed on Aug. 3, 2010, 4 pages.
Kang et al., PNAS USA (2006) 103(5):1289-1294.
Pietersz et al., Immunol. Rev. (1992) 129:57.
Prescott, (ed.), Methods in Cell Biology, XIV, p. 33, Academic Press, New York, (1976).
Rowlinson-Busza et al., Curr. Opin. Oncol. (1992) 4:1142.
Trail et al., Science (1993) 261:212.

(Continued)

*Primary Examiner* — James D Anderson
(74) *Attorney, Agent, or Firm* — Morrison & Foerster LLP

(57) ABSTRACT

The invention provides methods that relate to a novel therapeutic strategy for the treatment of hematological malignancies and inflammatory diseases. In particular, the method comprises administration of a compound of formula I,

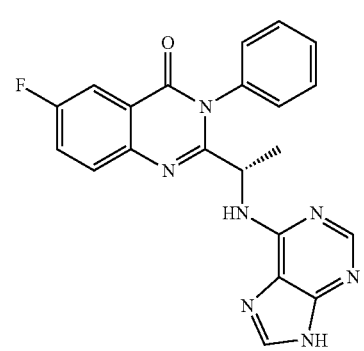

or a pharmaceutically acceptable salt thereof, or a pharmaceutical composition comprising such compound admixed with at least one pharmaceutically acceptable excipient.

25 Claims, 8 Drawing Sheets

(56) References Cited

U.S. PATENT DOCUMENTS

| | | | |
|---|---|---|---|
| 2004/0138199 A1 | 7/2004 | Goglietti et al. | |
| 2004/0242631 A1 | 12/2004 | Garlich et al. | |
| 2004/0248953 A1 | 12/2004 | Gogliotti et al. | |
| 2004/0248954 A1 | 12/2004 | Gogliotti et al. | |
| 2004/0259926 A1 | 12/2004 | Bruendle et al. | |
| 2005/0004195 A1 | 1/2005 | Para et al. | |
| 2005/0020630 A1 | 1/2005 | Connolly et al. | |
| 2005/0020631 A1 | 1/2005 | Gogliotti et al. | |
| 2005/0043239 A1 | 2/2005 | Douangpanya et al. | |
| 2005/0054614 A1 | 3/2005 | Diacovo et al. | |
| 2005/0112707 A1* | 5/2005 | Altaba et al. | 435/7.23 |
| 2005/0239809 A1 | 10/2005 | Watts et al. | |
| 2005/0261317 A1 | 11/2005 | Sadhu et al. | |
| 2006/0079538 A1* | 4/2006 | Hallahan et al. | 514/263.21 |
| 2006/0106038 A1 | 5/2006 | Bouscary et al. | |
| 2008/0275067 A1 | 11/2008 | Fowler et al. | |
| 2008/0287469 A1 | 11/2008 | Diacovo et al. | |
| 2008/0312199 A1* | 12/2008 | Glinsky | 514/170 |
| 2010/0029693 A1 | 2/2010 | Douangpanya et al. | |
| 2010/0152211 A1 | 6/2010 | Sadhu et al. | |
| 2010/0168139 A1 | 7/2010 | Sadhu et al. | |
| 2010/0202963 A1 | 8/2010 | Gallatin et al. | |
| 2010/0249155 A1 | 9/2010 | Evarts et al. | |
| 2010/0256167 A1 | 10/2010 | Fowler et al. | |
| 2010/0256168 A1 | 10/2010 | Fowler et al. | |
| 2011/0044942 A1 | 2/2011 | Puri et al. | |
| 2011/0230465 A1 | 9/2011 | Stammers et al. | |
| 2012/0015964 A1 | 1/2012 | Fowler et al. | |
| 2012/0040980 A1 | 2/2012 | Huggins et al. | |
| 2012/0135994 A1 | 5/2012 | Sadhu et al. | |
| 2012/0172591 A1 | 7/2012 | Sadhu et al. | |

FOREIGN PATENT DOCUMENTS

| | | |
|---|---|---|
| EP | 0 675 124 A2 | 10/1995 |
| EP | 0 675 124 A3 | 10/1995 |
| EP | 0 716 857 A1 | 6/1996 |
| EP | 0 716 857 B1 | 6/1996 |
| EP | 0 884 310 A1 | 12/1998 |
| EP | 0 884 310 B1 | 12/1998 |
| EP | 0 900 568 A2 | 3/1999 |
| EP | 0 900 568 A3 | 3/1999 |
| GB | 1356763 A | 6/1974 |
| GB | 2 017 097 A | 10/1979 |
| JP | 55 118917 A2 | 9/1980 |
| JP | 55 118918 A2 | 1/1981 |
| JP | 56 002322 A2 | 1/1981 |
| WO | WO-93/21259 A1 | 10/1993 |
| WO | WO-94/17090 A1 | 8/1994 |
| WO | WO-95/24379 A1 | 9/1995 |
| WO | WO-96/04923 A1 | 2/1996 |
| WO | WO-96/25488 A1 | 8/1996 |
| WO | WO-96/32478 A1 | 10/1996 |
| WO | WO-97/34631 A1 | 9/1997 |
| WO | WO-97/41097 A2 | 11/1997 |
| WO | WO-97/43276 A1 | 11/1997 |
| WO | WO-97/46688 A1 | 12/1997 |
| WO | WO-98/33802 A1 | 8/1998 |
| WO | WO-98/38173 A1 | 9/1998 |
| WO | WO-99/08501 A1 | 2/1999 |
| WO | WO-99/08501 A3 | 2/1999 |
| WO | WO-99/34804 A1 | 7/1999 |
| WO | WO-01/00881 A1 | 1/2001 |
| WO | WO-01/30768 A1 | 5/2001 |
| WO | WO-01/30768 C2 | 5/2001 |
| WO | WO-01/53266 A1 | 7/2001 |
| WO | WO-01/57034 A1 | 8/2001 |
| WO | WO-01/81346 A2 | 11/2001 |
| WO | WO-01/81346 A3 | 11/2001 |
| WO | WO-03/035075 A1 | 5/2003 |
| WO | WO-03/106622 A2 | 12/2003 |
| WO | WO-03/106622 A3 | 12/2003 |
| WO | WO-2004/007491 A1 | 1/2004 |
| WO | WO-2004/012768 A1 | 2/2004 |
| WO | WO-2004/026285 A2 | 4/2004 |
| WO | WO-2004/026285 A3 | 4/2004 |
| WO | WO-2004/029055 A1 | 4/2004 |
| WO | WO-2004/052373 A1 | 6/2004 |
| WO | WO-2004/056820 A1 | 7/2004 |
| WO | WO-2004/089925 A1 | 10/2004 |
| WO | WO-2004/108708 A1 | 12/2004 |
| WO | WO-2004/108709 A1 | 12/2004 |
| WO | WO-2004/108713 A1 | 12/2004 |
| WO | WO-2004/108713 C1 | 12/2004 |
| WO | WO-2004/108715 A1 | 12/2004 |
| WO | WO-2004/108715 C1 | 12/2004 |
| WO | WO-2005/016348 A1 | 2/2005 |
| WO | WO-2005/016349 A1 | 2/2005 |
| WO | WO-2005/067901 A2 | 7/2005 |
| WO | WO-2005/067901 A3 | 7/2005 |
| WO | WO-2005/113556 | 12/2005 |
| WO | WO-2005/117889 | 12/2005 |
| WO | WO-2005/120511 | 12/2005 |
| WO | WO-2005/120511 A1 | 12/2005 |
| WO | WO-2006/089106 | 8/2006 |
| WO | WO-2009/058361 A1 | 5/2009 |
| WO | WO-2010/065923 A2 | 6/2010 |
| WO | WO-2010/065923 A3 | 6/2010 |
| WO | WO-2010/123931 A1 | 10/2010 |

OTHER PUBLICATIONS

Written Opinion of the International Searching Authority for PCT/US2010/031794, mailed on Aug. 3, 2010, 6 pages.
Zhichkin et al., Organic Letters (2007) 9(7):1415-1418.
"Acute Congestive Heart Failure", Thomas N. Levin, Postgraduate Medicine, vol. 101, No. 1, 1997.
Sutton, A. (Jun. 9, 2006). "Baylor, St. Luke's study uses gene therapy as pancreatic cancer", located at <http: //www.bcm.edu/news/item.cfm?newsID=640>, last visited on Sep. 2, 2006, 2 pages.
Anonymous (2006). "Cardiovascular Disease: Treatment for Stroke", Stanford Hospital & Clinics, located at <http://www.stanfordhospital.com/healthLib/atoz/cardiac/stktreat.html>, last visited on Sep. 19, 2006, 2 pages.
Marchione et al. (2006). "Drugs hold promise in kidney cancer fight", located at <http://www.ledger-enquirer.com/mld/ledgerenquirer/living/health/14744763.htm>, last visited on Sep. 2, 2006, 3 pages.
Anonymous (2006). "Heart Disease", WebMD, located at <http://www.webmd.com/content/pages/9/167557842.htm> as retrieved on Sep. 14, 2006, 1 page.
Anonymous, (2010). "Multiple Sclerosis", located at <http://www.health.nytimes.com/health/quides/disease/multiple-sclerosis/overview.html>, last visited Aug. 1, 2010, 4 pages.
Anonymous, (2004). "NIH Heart Disease & Stroke Research: Fact Sheet", American Heart Association, located at <http://www.americanheart.org/presenter.jhtml?identifier=3010188>, last visited Feb. 17, 2004, 1 page.
Anonymous (2010). "Spinal Cord Injury", located at <http://www.medicinenet.com/spinal_cord_injury/page,htm>, last visited on Aug. 1, 2010, 3 pages.
Anonymous (2010) "Systemic Lupus Erythematosus", located at <http://www.nlm.nih.gov/medlineplus/ency/article/000435.htm, last visited Aug. 1, 2010, 4 pages.
"Chemia Leków", ed. E. Pawelczyk, PZWL, Warszawa 1986, see, part 1.2.2.
"Preparatyka Organiczna", ed. A.I. Vogel, WNT, Warszawa 1984, p. e.g. 83.
Abu-Duhier et al., Br. J. Haematol. (2001) 113:983-988.
Adamkiewicz, "Tumor Angiogenesis: Mechanisms" IMT Marburg—Research Group, retrieved from the internet on Apr. 13, 2004, located at: <http://www.imt.uni-marburg.de/~adamkiew/mechanism.html>, 2 pages.
Advisory Action from U.S Appl. No. 11/596,092, mailed on Jul. 27, 2010.
Ager et al., J. Med. Chem. (1977) 20:379-386.
Ali et al., Nature (2004) 431:1007-1011.
Alon et al., "The molecular basis of leukocyte adhesion to and migration through vascular endothelium," Mirelman et al. (eds.), Life Sciences Open Day Book 2002, Weizmann Institute of Science, Life Sciences Department, Chapter 8, vol. 2:206-207 (2002), retrieved from the internet on Sep. 2, 2005, located at <http://www.weizmann.ac.il/Biology/open_day_2002/book/ronen_alon.pdf>, 2 pages.

Amendment from U.S. Appl. No. 09/841,341, filed Aug. 21, 2002.
Amendment from U.S. Appl. No. 10/027,591, filed Jun. 3, 2003.
Amendment in Response to Final Office Action from U.S. Appl. No. 11/596,092, filed Jul. 19, 2010.
Amendment in Response to Non-Final Office Action / Restriction Requirement from U.S. Appl. No. 11/884,566, filed Jun. 7, 2010.
Amendment in Response to Non-Final Office Action from U.S. Appl. No. 10/918,803, filed on Oct. 1, 2008.
Amendment in Response to Non-Final Office Action from U.S. Appl. No. 10/918,803, filed Sep. 4, 2009.
Amendment in Response to Non-Final Office Action from U.S. Appl. No. 11/110,204, filed Dec. 31, 2008.
Amendment in Response to Non-Final Office Action from U.S. Appl. No. 11/110,204, filed Sep. 4, 2009.
Amendment in Response to Non-Final Office Action from U.S. Appl. No. 11/110,204, filed Jun. 4, 2010.
Amendment in Response to Non-Final Office Action from U.S. Appl. No. 11/596,092, filed on Nov. 10, 2009.
Amendment in Response to Non-Final Office Action from U.S. Appl. No. 11/596,092, filed Mar. 24, 2010.
Amendment Under 37 C.F.R. § 1.111 from U.S. Appl. No. 11/129,006, filed on Apr. 12, 2010.
Amendment Under 37 C.F.R. § 1.111/Restriction Requirement from U.S. Appl. No. 11/110,204, filed Apr. 10, 2008.
Amendment with Request for Continued Examination from U.S. Appl. No. 11/596,092, filed Sep. 1, 2010.
Amin et al., Circ Res (2003) 93(4):321-329.
Angel, Activities of Phosphoinositide Kinase-3 (PI3K) (1999) retrieved from the internet on May 22, 2003, URL: http://www.chem.csustan.edu/chem4400/SJBR/ange199.htm.
Angio World, "How Angiogenesis Complicates Psoriasis" (2001) retrieved from the internet on Apr. 13, 2004, located at <http://www.angioworld.com/psoriasis.htm,1 page.
Annabi et al., J. Cell. Biochem. (2004) 91:1146-1158.
Aoki et al., PNAS USA (2001) 98:136-141.
Aoudjit et al., J. Immunol. (1998) 161:2333-2338.
Arcaro et al., Biochem. J. (1994) 298:517-520.
Asti et al., Pulm. Pharmacol. Ther. (2000) 13:61-69.
Ausprunk et al., Microvasc. Res. (1977) 14:53-65.
Bader, A.G. et al. (2005). "Oncogenic PI3K Deregulates Transcription and Translation," Nature Reviews Cancer 5(12):921-922 (abstract and introduction).
Barakat et al., Chemical Abstracts (1996) 124(21):1334.
Barakat, S.E-S. et al. (Dec. 1994). "Synthesis and CNS Depressant Activity of Some New Quinazoline Derivatives," Az. J. Pharm. Sci. 14:239-246.
Bardet et al., 9th Congress of the European Hematology Association Geneva Palexpo, Switzerland, Jun. 10-13, 2004, View Abstract data, Abstract nr.: 620.
Barker, Lancet (1991) 338:227-230.
Benekli et al., Blood (2002) 99:252-257.
Benekli et al., Blood (2003) 101:2940-2954.
Bennett et al., Ann. Intern. Med. (1985) 103:620-625.
Bennett et al., J. Pharmacol. Exp. Ther. (1997) 280:988-1000.
Bergers et al., Science (1999) 284:808-812.
Bharadwaj et al., J. Immunol. (2001) 166:6735-6741.
Binetruy-Tournaire et al., Embo J. (2000) 19:1525-1533.
Bloemen et al., Am. J. Respir. Crit. Care Med. (1996) 153:521-529.
Boehm et al., Nature (1997) 390:404-407.
Borregaard et al., Blood (1997) 89:3503-3521.
Boudewijn et al., Nature (1995) 376:599-602.
Bouscary et al., Blood (2003) 101:3436-3443.
Bouscary et al., Oncogene (2001) 20:2197-2204.
Bowes et al., Exp. Neurol. (1993) 119:215-219.
Brennan et al., Arthritis Res. (2002) 4(Suppl. 3):S177-S182.
Brown et al., 44th Annual Meeting of the American Society of Hematology, Philadelphia, PA, Dec. 6-10, 2002, Abstract No. 3012, p. 761A.
Brown, J. et al. (2010). "Clinical Activity in a Phase 1 Study of Cal-101, an Isoform-Selective Inhibitor of Phosphatidylinositol 3-Kinase P110Delta, in Patients with B-Cell Malignancies," Haematologica 95(s2):466, Abstract No. 1130.
Brunn et al., EMBO J. (1996) 15:5256-5267.

Burgering et al., Nature (1995) 376:599-602.
Butcher et al., Science (1996) 272:60-66.
Cadwallader et al., J. Immunol. (2002) 169:3336-3344.
Cantley et al., PNAS USA (1999) 96:4240-4245.
Cantley et al., Science (2002) 296:1655-1657.
Cardone et al., Science (1998) 282:1318-1321.
Carnero et al., FEB Letters (1998) 422:155-159.
CAS Abstract, Accession No. DN 86:83505 [1977] pp. 112-118.
Cebon et al., Cancer Immun. (2003) 3:7-25.
Chang et al., Exp. Opin. Ther. Patents (2001) 11:45-59.
Chang, BioMed. Eng. Online (2003) 2:12.
Chen et al., Blood (2000) 96:3181-3187.
Chern et al., Chem. Pharm. Bull. (1998) 46(6):928-933.
Chern et al., Chemical Abstracts (1998) 129(16):676.
Chopp et al., Stroke (1994) 25:869-876.
Choy et al., Arthritis & Rheumatism (2002) 46:3143-3150.
Clark et al., J. Neurosurg. (1991) 75:623-627.
Clavel et al., Joint Bone Spine (2003) 70:321-326.
Clayton et al., J. Exp. Med. (2002) 196:753-763.
Cleary, J.M. et al. (2010). "Development of Phosphoinositide-3 Kinase Pathway Inhibitors for Advanced Cancer," Curr. Oncol. Rep. 12:87-94.
Coligan et al., Current Protocols in Protein Science (2002) 3:15-20.
Constantin et al., Immunity (2000) 13:759-769.
Cosimi et al., J. Immunol. (1990) 144:4604-4612.
Coxon, Immunity (1996) 5:653-666.
Creamer et al., Angiogenesis (2002) 5:231-236.
Cross et al., Inflamm. Res. (1999) 48:255-261.
Curnock et al., Immunology (2002) 105:125-136.
Dahia et al., Hum. Mol. Genet. (1999) 8:185-193.
Dallegri et al., Inflamm. Res. (1997) 46:382-391.
Das et al., Prog. Retin. Eye Res. (2003) 22:721-748.
Datta et al., Cell (1997) 91:231-241.
Datta et al., Genes & Dev. (1999) 13:2905-2927.
Davies et al., Biochem. J. (2000) 351:95-105.
De Benedetti et al., Clin. Exper. Reheum. (1992) 10:493-498.
Deininger et al., Blood (2000) 96:3343-3356.
Demeester et al., Transplantation (1996) 62:1477-1485.
Descamps et al., J. Immunol. (2004) 173:4953-4959.
Doggett et al., Biophys. J. (2002) 83:194-205.
Dorland's Illustrated Medical Dictionary (2003), retrieved Oct. 21, 2005 from Xreferplus, http://www.xreferplus.com/entry/4196914.
Downward, Nature (1995) 376:553-554.
Drakesmith et al., Immunol. Today (2000) 21:214-217.
Druker et al., New England Journal of Medicine (2001) 344:1038-1042.
Dunne et al., Blood (2002) 99:336-341.
Edwards et al., Canc. Res. (2002) 62:4671-4677.
Eichholtz et al., J. Biol. Chem. (1993) 268:1982-1986.
El-Fattah et al., Indian J Hetercyclic Chemistry (1995) 4:199-202.
El-Feky, S.A. et al. (1985). "Synthesis of Certain New Sulfur-Containing Quinazolinone Derivatives Likely to Possess CNS Depressant Action," Egyptian Journal of Pharmaceutical Sciences 24(1-4):39-47.
El-Feky et al., Chemical Abstracts (1987) 106(13):650.
El-Feky et al., Chemical Abstracts (1999) 131(23):497.
El-Feky, S.A. (Aug. 1998). "Novel Quinazolinones From 2-Cyanomethyl-3-Phenyl-4(3H) Quinazolinone," Bollettino Chimico Farmaceutico 137(7):286-289.
Engelman et al., Nature Reviews (2006) 7:606-619.
Environmental Protection Agency, EPA-Radiation Information (EPA's Radiation Protection Program:Information) "Ionizing Radiation Fact Sheet Series No. 1" (May 1998) Retrieved on Apr. 21, 2004: http://www.epa.gov/radiation/docs/ionize/ionize.htm.
Erbagci et al., Clin. Biochem. (2001) 34:645-650.
Estey, Cancer (2001) 92:1059-1073.
Etzioni, Pediatr. Res. (1996) 39:191-198.
European Search Report mailed Mar. 29, 2011, for EP Patent Application No. 10163434.3, filed on Apr. 24, 2001, 9 pages.
Faffe et al., Eur. Respir. J. (2000) 15:85-91.
Fantl et al., Ann. Rev. Biochem. (1993) 62:453-481.
Faust et al., Blood (2000) 96:719-726.

Final Office Action from U.S. Appl. No. 10/918,803, mailed on Jan. 8, 2009.
Final Office Action from U.S. Appl. No. 11/129,006, mailed on Oct. 5, 2010.
Final Office Action from U.S. Appl. No. 11/596,092, mailed on May 18, 2010.
Final Office Action mailed on Oct. 24, 2011, for U.S. Appl. No. 12/732,128, filed Mar. 25, 2010, 8 pages.
Final Office Action mailed on Feb. 15, 2012, for U.S. Appl. No. 12/732,124, filed Mar. 25, 2010, 12 pages.
Final Office Action mailed on Jun. 7, 2012, for U.S. Appl. No. 11/129,006, filed May 12, 2005, 14 pages.
First Preliminary Amendment from U.S. Appl. No. 12/538,748, filed Apr. 1, 2010.
Flinn, I.W. et al. (2009). "Preliminary Evidence of Clinical Activity in a Phase 1 Study of CAL-101, a Selective Inhibitor of the p110δ Isoform of Phosphatidylinositol 3-Kinase (P13K), in Patients with Select Hematologic Malignancies," *Journal of Clinical Oncology* 27:156s, Abstract 3543.
Flinn, I.W. et al. (Nov. 20, 2009). "Evidence of Clinical Activity in a Phase 1 Study of CAL-101, an Oral P110Δ Isoform-Selective Inhibitor of Phosphatidylinositol 3-Kinase, in Patients with Relapsed or Refractory B-Cell Malignancies," *Blood* 114(22):380, Abstract 922.
Flinn, W. et al. (Jun. 4-7, 2009). "Preliminary Evidence of Clinical Activity in a Phase 1 Study of CAL-101, A Potent Selective Inhibitor of the P110Delta Isoform of Phosphatidylinositol 3-Kinase, in Patients with B-Cell Maglignancies," *Haematologica* 94(s2):303, Abstract 0744.
Folkman, Curr. Mol. Med. (2003) 3:643-651.
Folkman, Nat. Med. (1995) 1:27-31.
Fraser et al., Science (1991) 251:313-316.
Frey et al., Lancet (2008) 372(9643):1088-1099 (abstract).
Freyssinier et al., Br. J. Haematol. (1999) 106:912-922.
Fruman et al., Ann. Rev. Biochem. (1998) 67:481-507.
Fruman et al., Semin. Immunol. (2002) 14:7-18.
Furman, R.R. (Jul. 2010). "New Agents in Early Clinical Trials for CLL Therapy," *Clinical Advances in Hematology & Oncology* 8(7):475-476.
Garcia-Barros et al., Science (2003) 300:1155-1159.
Genbank Accession No. AK040867, last updated Sep. 19, 2008, located at <http://www.ncbi.nlm.nih.gov.nuccore/26334014>, last visited on Apr. 16, 2010, 6 pages.
GenBank Accession No. AR255866, last updated Dec. 20, 2002, located at <http://www.ncbi.nlm.nih.gov.nuccore/27305059>, last visited on Apr. 16, 2010, 2 pages.
GenBank Accession No. BC035203, last updated Aug. 11, 2006, located at <http://www.ncbi.nlm.nih.gov/nuccore/23270986>, last visited on Apr. 16, 2010, 5 pages.
GenBank Accession No. NM_005026, last updated Apr. 11, 2010, located at <http://www.ncbi.nlm.nih.gov/nuccore/15654404>, last visited Apr. 16, 2010, 7 pages.
GenBank Accession No. NM_008840, last updated on Mar. 5, 2010, located at <http://www.ncbi.nlm.nih.gov/nuccore/255708435>, last visited on Apr. 16, 2010, 5 pages.
GenBank Accession No. U57843, last updated on May 9, 1997, located at <http://www.ncbi.nlm.nih.gov/nuccore/U57843>, last visited on Aug. 9, 2011, 2 pages.
GenBank Accession No. U86453, last updated on Jul. 7, 1998, located at <http://www.ncbi.nlm.nih.gov/nuccore/2317893>, last visited on Apr. 16, 2010, 3 pages.
GenBank Accession No. U86587, last updated Jul. 7, 1998, located at <http://www.ncbi.nlm.nih.gov/nuccore/2331237>, last visited on Apr. 16, 2010, 3 pages.
GenBank Accession No. XM_345606, last updated Jun. 22, 2006, located at <http://www.ncbi.nlm.nih.gov/nuccore/109475856?report=genbank>, last visited on Apr. 16, 2010, 3 pages.
GenBank Accession No. Y10055, last updated Oct. 7, 2008, located at <http://www.ncbi.nlm.nih.gov/nuccore/37496958>, last visited on Apr. 16, 2010, 3 pages.
Geng et al., Cancer Research (2001) 61:2413-19.
Geng et al., Cancer Research (2004) 64:4893-4899.
Geng et al., Cancer Research (2004) 64:8130-8133.
Gibson, (ed.), Antisense and Ribozyme Methodology, "Laboratory Companion" (1997) Table of Contents.
Gilliland et al., Blood (2002) 100:1532-1542.
Gilliland et al., Cancer Cell (2002) 1:417-420.
Gingras et al., Genes Dev. (2001) 15:2852-2864.
Gingras et al., Genes Dev. (2001) 15:807-826.
Glenjen et al., Int. J. Cancer (2002) 101:86-94.
Gorczynski et al., J. Immunol. (1994) 152:2011-2019.
Gorski et al., Cancer Research (1999) 59:3374-3378.
Gouilleux-Gruart et al., Blood (1996) 87:1692-1697.
Grant et al., Drugs of Today (2002) 38:783-791.
Gross et al., Science (1998) 281:703-706.
Gu et al., Mol. Cell. Biol. (2000) 20:7109-7120.
Gupta et al., Int'l J Radiation Oncology Biology Physics (2003) 56(3):846-853.
Gute et al., Mol. Cell. Biochem. (1998) 179:169-187.
Guzman et al., Blood (2001) 98:2301-2307.
Guzman et al., Proc. Natl. Acad. Sci. (USA) (2002) 99:16220-16225.
Hadden, Int. Immunopharmacol. (2003) 3:1061-1071.
Hallahan et al., Proc. Natl. Acad. Sci (USA) (1997) 94:6432-6437.
Halloran et al., Arthritis Rheum. (1996) 39:810-819.
Hanamoto et al., Am. J. Pathol. (2004) 164(3):997-1006.
Hannigan et al., Proc. Natl. Acad. Sci. U.S.A. (2002) 99:3603-3608.
Hardma et al. (eds.), Goodman and Gilman's The Pharmacological Basis of Therapeutics (1996) 9th ed., pp. 11-16.
Harlan, Haematology 96, the Education Program Book of the 26th Congress of the International Society of Haematology. Singapore, 1996.
Harning et al., Transplantation (1991) 52:842-845.
Hartley et al., Cell (1995) 82:849-856.
Hartman et al., Cardiovasc. Res. (1995) 30:47-54.
Hasagawa et al., Int. Immunol. (1994) 6:831-838.
Hassan et al., Chinese Journal of Chemistry (1991) 9:262-269.
Hattori, H. et al. (May/Jun. 2010). "Reactive Oxygen Species as Signaling Molecules in Neutrophil Chemotaxis," *Communicative and Integrative Biology* 3(3):278-281.
He et al., Opthalmol. Vis. Sci. (1994) 35:3218-3225.
Healy et al., Hum. Reprod. Update (1998) 4:736-740.
Healy et al., Pharma. Res. (Dec. 2004) 21:2234-2246.
Heit et al., J. Cell Biol. (2002) 159:91-102.
Hellman, Cancer: Principles and Practice of Oncology (1993) 4th ed., vol. 1:248-275.
Herman, S.E.M. et al. (Sep. 23, 2010). "Phosphatidylinositol 3-Kinase-δ Inhibitor CAL-101 Shows Promising Preclinical Activity in Chronic Lymphocytic Leukemia by Antagonizing Intrinsic and Extrinsic Cellular Survival Signals," *Blood* 116(12):2078-2088.
Herold et al., Cell Immunol. (1994) 157:489-500.
Higuchi, Prodrugs as Novel Delivery Systems, vol. 14, ASCD Symposium Series, and in Roche (ed.), Bioreversible Carriers in Drug Design, American Pharmaceutical Association and Pergamon Press (1987) Chapter 1, pp. 1-12.
Hilbert et al., J. Exper. Med. (1995) 182:243-248.
Hiles et al., Cell (1992) 70:419-429.
Hilmas et al., Rad. Res. (1975) 61:128-143.
Hirsch et al., Science (2000) 287:1049-1053.
Horgan et al., Am. J. Physiol. (1991) 261:H1578-H1584.
Hsieh, Friedrick Schiller University, Jena, Germany (2003).
Hu et al., Mol. Cell. Biol. (1993) 13:7677-7688.
Hu et al., Science (1995) 268:100-102.
Hunter, Cell (1995) 83:1-4.
Hussong et al., Blood (2000) 95:309-313.
Ikeda, H. et al. (Feb. 2009). "CAL-101: A Selective Inhibitor of P13K p110δ for the Treatment of Multiple Myeloma," *Clinical Lymphoma and Myeloma* 9(Supp.1):S98-S99.
Ikeda, H. et al. (Nov. 16, 2008). "CAL-101, a Specific Inhibitor of the p110δ Isoform of Phosphatidylinositide 3-Kinase Induces Cytotoxicity in Multiple Myeloma (MM)," *Blood* 112(11):950, Abstract No. 2753.
Ikeda, H. et al. (Sep. 2, 2010). "PI3K/p110δ is a Novel Therapeutic Target in Multiple Myeloma," *Blood* 116(9):1460-1468.
International Preliminary Report on Patentability for PCT/US2006/005621, issued on Aug. 21, 2007, 8 pages.

International Search Report for International (PCT) Patent Application Serial No. PCT/US2004/026436, dated Dec. 2, 2004.
International Search Report for International (PCT) Patent Application Serial No. PCT/US2004/029561, dated May 25, 2005.
International Search Report for International (PCT) Patent Application Serial No. PCT/US2004/026834, dated Nov. 29, 2004.
International Search Report for International (PCT) Patent Application Serial No. PCT/US2004/037860, dated May 6, 2005.
International Search Report mailed on Aug. 29, 2005, for PCT Application No. PCT/US2005/016778, filed on May 12, 2005, 4 pages.
International Search Report mailed on Sep. 15, 2006 for PCT Application No. PCT/US2006/005621, filed on Feb. 16, 2006, 4 pages.
Interview Summary from U.S. Appl. No. 10/918,825, mailed on Jun. 14, 2006.
Ismail and Sayed, Indian Journal of Chemistry (1982) 21 B(5):461-462.
Ismail et al., Chemical Abstracts (1983) vol. 98, No. 1, p. 406.
Isobe et al., Science (1992) 255:1125-1127.
Johnson et al., Intl. J. Rad. One. Biol. Phys. (1976) 1:659-670.
Johnson et al., J. Endourol. (2003) 17:557-562.
Jordan, Nature Reviews: Drug Discovery (2003) 2:205.
Jou et al., Mol. Cell. Biol. (2002) 22:8580-8591.
Kahl, B.S. (May 2010). "Novel Agents for Non-Hodgkin Lymphoma," *Clinical Advances in Hematology & Oncology* 8(5)(Suppl. 10):10-15.
Kakimoto et al., Cell. Immunol. (1992) 142:326-337.
Kallman et al., Canc. Res. (1972) 32:483-490.
Kandel et al., Exp. Cell Res. (1999) 253:210-229.
Kawasaki et al., J. Immunol. (1993) 150:1074-1083.
Kim et al., Endocrin. (2000) 141:1846-1853.
Kim, Retrieved from the Internet on Apr. 13, 2004: URL: http://www.math.umn.edu/~yjkim/biopaper/timy,html.
Kishimoto et al., Cell (1987) 50:193-202.
Klein et al., Cell. Signal. (2001) 13:335-343.
Klippel et al., Mol. Cell. Biol. (1994) 14:2675-2685.
Knall et al., Proc. Natl. Acad. Sci. (USA) (1997) 94:3052-3057.
Knight and Shokat, Chemistry and Biology (2005) 12:621-637.
Knight et al., Bioorganic & Medicinal Chemistry (Jul. 2004) 12:4749-4759.
Knoerzer et al., Toxicol. Pathol. (1997) 25:13-19.
Kolonin et al., Nature Medicine (2004) 10:625-632.
Kong et al., J. Biol. Chem. (2000) 275:36035-36042.
Kopf et al., Nature (1994) 368:339-342.
Krugmann et al., J. Biol. Chem. (1999) 274:17152-17158.
Kumar et al., Blood (2003) 101(10):3960-3968.
Kunkel et al., Circ. Res. (1996) 79:1196-1204.
Lannutti, B.J. et al. (Apr. 2009). "CAL-101, a Specific PI3K p110δ Inhibitor for the Treatment of Hematological Maglignancies," *Proceedings of the American Association for Cancer Research* 50:1400, Abstract No. #SY32-2.
Lannutti, B.J. et al. (Nov. 16, 2008). "CAL-101, a Potent Selective Inhibitor of the p110d Isoform of Phosphatidylinositol 3-Kinase, Attenuates PI3K Signaling and Inhibitos Proliferation and Survival of Acure Lumpoblastic Leukemia in Addition to a Range of Other Hematological Malignancies," *Blood* 112(11):12, Abstract No. 16.
Lannutti, B.J. et al. (Nov. 20, 2009). "CAL-101, An Oral P110δSelective Phosphatidylinositol-3-Kinase (PI3K) Inhibitor for the Treatment of B Cell Malignancies Inhibits PI3K Signaling, Cellular Viability and Protective Signals of the Microenvironment," *Blood* 114(22):120-121, Abstract No. 286.
Lannutti, J. et al. (2010). "Demonstration of Pharmacodynamic Target Inhibition and Chemokine Modulation in Patients with CLL Following Treatment with CAL-101, a Selective Inhibitor of the P110 Delta Isoform of PI3K," *Haematologica* 95(52):45-46, Abstract No. 0113.
Lannutti, J. et al. (Jun. 4-7, 2009). "CAL-101, A Specific Inhibitor of the P11-Delta Isoform of Phosphatidylinositide 3-Kinase, for the Treatment of Non-Hodgkins Lymphomas," *Haematologica* 94(52):272-273, Abstract No. 0668.
Lecoq-Lafon et al., Blood (1999) 93:2578-2585.
Lemmon et al., Trends Cell. Biol. (1997) 7:237-242.
Letter from Polish Patent Law Firm "Patpol" translating Office Action from Polish Patent Application No. P-358590, dated Feb. 27, 2008.
Li et al., Trends Biochem. Sci. (Jan. 2004) 29:32-38.
Liang et al., Molecular Cancer Therapeutics (2003) 2(4):353-360.
Liekens et al., Biochem. Pharmacol. (2001) 61:253-270.
Liu et al., J. Immunol. (Jan. 2004) 172 :7-13.
Lowell et al., J. Cell Biol. (1996) 133:895-910.
Luo et al., Cancer Cell (2003) 4:257-262.
Luo et al., Leukemia (2003) 17:1-8.
Luster, N. Engl. J. Med. (1998) 338:436-445.
Madge et al., J. Biol. Chem. (2000) 275:15458-15465.
Manning et al., Mol. Cell (2002) 10:151-162.
Marley et al., Br. J. Haematol. (May 2004) 125:500-511.
May, S.E. et al. (Nov. 16, 2008). "CAL-101, a Selective Inhibitor of the p110δ Isoform of Phosphatidylinositol 3-Kinase, Effectively Induces Apoptosis in Primary Chronic Lumphocytic Leukemia Cells Providing a Novel Therapeutic Strategy for the Treatment of this Disease," *Blood* 112(11):1085-1086, Abstract No. 3165.
Meneses et al., Gene Ther. (2001) 8:646-648.
Milella et al., J. Clin. Invest. (2001) 108:851-859.
Miller et al., Nucleic Acids Res. (1988) 16:1215.
Moehler et al., Ann. Hematol. (2001) 80:695-705.
Moore, J. Clin. Invest. (2002) 109:313-315.
Moulton et al., Circ. (1999) 99:1726-1732.
Mulligan et al., J. Immunol. (1995) 154:1350-1363.
Mulligan et al., Proc. Natl. Acad. Sci. (USA) (1993) 90:11523-11527.
Nagase et al., Am. J. Respir. Crit. Care Med. (1996) 154:504-510.
Nakao et al., Leukemia (1996) 10:1911-1918.
Nakao et al., Muscle Nerve (1995) 18:93-102.
Neshat et al., Proc. Natl. Acad. Sci. (USA) (2001) 98:10314-10319.
Ninomiya et al., J. Biol. Chem. (1994) 269:22732-22737.
Non Final Office Action from U.S. Appl. No. 11/596,092, mailed on Dec. 24, 2009.
Non-Final Office Action from U.S. Appl. No. 09/841,341, mailed on Apr. 25, 2002.
Non-Final Office Action from U.S. Appl. No. 10/027,591, mailed on Feb. 26, 2003.
Non-Final Office Action from U.S. Appl. No. 10/918,803, mailed on Apr. 1, 2008.
Non-Final Office Action from U.S. Appl. No. 10/918,803, mailed on Mar. 16, 2010.
Non-Final Office Action from U.S. Appl. No. 10/918,825, mailed on Nov. 7, 2005.
Non-Final Office Action from U.S. Appl. No. 11/110,204, mailed on Aug. 5, 2008.
Non-Final Office Action from U.S. Appl. No. 11/110,204, mailed on Feb. 4, 2010.
Non-Final Office Action from U.S. Appl. No. 11/110,204, mailed on Jun. 17, 2009.
Non-Final Office Action from U.S. Appl. No. 11/129,006, mailed on Dec. 15, 2009.
Non-Final Office Action mailed on Jan. 20, 2012 for U.S. Appl. No. 13/163,597, filed Jun. 17, 2011, 14 pages.
Non-Final Office Action mailed on Oct. 17, 2011 for U.S. Appl. No. 12/732,124, filed Mar. 25, 2010, 8 pages.
Non-Final Office Action from U.S. Appl. No. 11/596,092, mailed on Jun. 10, 2009.
Non-Final Office Action from U.S. Appl. No. 11/884,566, mailed on Aug. 3, 2010.
Non-Final Office Action mailed on Jun. 28, 2011, for U.S. Appl. No. 12/732,124, filed Mar. 25, 2010, 11 pages.
Non-Final Office Action mailed on Aug. 2, 2012 for U.S. Appl. No. 12/575,277, filed Oct. 7, 2009, 8 pages.
Non-Final Office Action mailed on Aug. 7, 2012 for U.S. Appl. No. 12/575,367, filed Oct. 7, 2009, 9 pages.
Notice of Allowance from U.S. Appl. No. 09/841,341, mailed on Oct. 7, 2002.
Notice of Allowance from U.S. Appl. No. 10/027,591, mailed on Jul. 29, 2003.
Notice of Allowance from U.S. Appl. No. 10/337,192, mailed on Mar. 11, 2004.

Notice of Allowance from U.S. Appl. No. 10/697,912, mailed on Dec. 30, 2004.
Notice of Allowance mailed on Nov. 8, 2010, for U.S. Appl. No. 11/110,204, filed Apr. 20, 2005, 6 pages.
Notice of Allowance mailed on Jun. 26, 2012 for U.S. Appl. No. 12/732,124, filed Mar. 25, 2010, 11 pages.
Notice of Reexamination for Chinese Patent Application No. 0811654.X, mailed Nov. 5, 2009; 7 pages.
Notice Regarding Non-Compliant Amendment from U.S. Appl. No. 10/918,803, mailed on Nov. 19, 2009.
Notification of Reasons for Rejection for Japanese Patent Application No. 2003-537642, mailed on May 26, 2009, 4 pages.
Office Action for European Patent Application No. 04 816 855.3, mailed on Oct. 21, 2008, 4 pages.
Office Action for European Patent Application No. 01 928 855.4, mailed on Feb. 26, 2009, 3 pages.
Office Action for European Patent Application No. 01 928 855.4, mailed on Nov. 15, 2007, 4 pages.
Office Action for European Patent Application No. 01 928 855.4, mailed on Mar. 29, 2006, 6 pages.
Office Action for European Patent Application No. 01 928 855.4, mailed on Jul. 13, 2004, 5 pages.
Office Action for European Patent Application No. 02 757 407.8, mailed on Oct. 6, 2009, 3 pages.
Office Action for European Patent Application No. 02 757 407.8, mailed on Jul. 1, 2009, 2 pages.
Office Action for European Patent Application No. 02 757 407.8, mailed on Oct. 21, 2008, 3 pages.
Office Action for European Patent Application No. 02 757 407.8, mailed on Jun. 6, 2007, 2 pages.
Office Action for European Patent Application No. 02 757 407.8, mailed on Jan. 24, 2006, 3 pages.
Office Action for European Patent Application No. 04 816 855.3, mailed on Feb. 2, 2011, 4 pages.
Office Action for European Patent Application No. 05 752 122.1, mailed on Dec. 28, 2010, 4 pages.
Office Action for European Patent Application No. 04 810 878.1, mailed on Sep. 10, 2010, 4 pages.
Ohno-Matsui et al., Invest. Ophthalmol. Vis: Sci. (2003) 44:5370-5375.
Okkenhaug et al., Science (2002) 297:1031-1034.
Oppenheimer-Marks et al., J. Clin. Invest. (1998) 101:1261-1272.
Oshiro et al., Stroke (1997) 28:2031-2038.
Otsu et al., Cell (1991) 65:91-104.
Paez et al., Frank (ed.), Cancer Treatment and Research (2003) 115:146 Kluwer Academic Publishers.
Pages et al., Nature (1994) 369:327-329.
Palanki, Curr. Med. Chem. (2002) 9:219-227.
Paleolog et al., Angiogenesis (1998/1999) 2:295-307.
Panayotou et al., Trends in Cell Biol. (1992) 2:358-360.
Panes et al., Gastroenterology (1995) 108:1761-1769.
Parasharya and Parikh, J. Inst. Chemists (1992) 64(5):184-185.
Parasharya et al., Chemical Abstracts (1994) vol. 121, No. 9, p. 1065.
Park, S. et al. (2010). "Role of the PI3K/AKT and mTOR Signaling Pathways in Acute Myeloid Leukemia," *Haematologica* 95(5):819-829.
Parker, Current Biology (1995) 5:577-579.
Passegue et al., Proc. Natl. Acad. Sci., (USA) (2003) 100 Supp. 1:11842-11849.
Patani, G.A. et al. (1996), "Bioisosterism: A Rational Approach in Drug Design," *Chem Rev.* 96(8):3147-3176.
Pierce et al., J. Biol. Chem. (1997) 272:21096-21103.
Plows et al., J. Immunol. (1999) 162(2):1018-1023.
Podsypanina et al., Proc. Natl. Acad. Sci. (USA) (2001) 98:10320-10325.
Psychoyos et al., J. Immunol. Methods (1991) 137:37-46.
Puri et al., Blood (2005) 106(1):150-157, 144.
Puri et al., Blood (May 2004) 103:3448-3456.
Puri, K. et al. (Jul. 18-23, 2004). "A Role for Phosphoinositide 3-Kinase δ in Neutrophil Trafficking," Immunology 2004: Cytokine Network, Regulatory Cells, Signaling, and Apoptosis: Collection of Free Papers Presented at the 12th International Congress of Immunology and 4th Annual Conference of FOCIS Medimond International Proceedings in Montreal, Canada on Jul. 18, 23, 2004, pp. 303-307.
Quirici et al., Br. J. Haematol. (2001) 115:186-194.
Rameh et al., Cell (1995) 83:821-830.
Rameh et al., J. Biol. Chem. (1999) 274:8347-8350.
Rathman et al., J. Org. Chem. (1980) 45:2169-2176.
Remington'S Pharmaceutical Sciences (1990) 18th Ed., Chapter 89, pp. 1435-1712 Table of Contents Only.
Ren et al., Curr. Drug Targets Inflamm. Allergy (2003) 2(3):242-256.
Request for Continued Examination and Amendment Under 37 C.F.R. § 1.116 from U.S. Appl. No. 10/918,803, filed May 7, 2009.
Response to Election of Species Requirement from U.S. Appl. No. 10/918,803, filed Jun. 27, 2007 (5.00).
Response to Non-Final Office Action from U.S. Appl. No. 10/918,803, filed Dec. 18, 2009.
Response to Non-Final Office Action filed on Sep. 16, 2010, for U.S. Appl. No. 10/918,803, filed Aug. 13, 2004, 25 pages.
Response to Restriction Requirement from U.S. Appl. No. 10/918,803, filed Jan. 4, 2008.
Response to Restriction Requirement from U.S. Appl. No. 11/129,006, filed May 12, 2009.
Response to Restriction Requirement from U.S. Appl. No. 11/137,901, filed Feb. 6, 2008.
Response to Restriction Requirement from U.S. Appl. No. 11/596,092, filed May 27, 2009.
Restriction Requirement from U.S. Appl. No. 10/918,803, mailed on Jun. 12, 2009.
Restriction Requirement from U.S. Appl. No. 10/918,803, mailed on Mar. 13, 2007.
Restriction Requirement from U.S. Appl. No. 10/918,803, mailed on Sep. 7, 2007.
Restriction Requirement from U.S. Appl. No. 11/110,204, mailed on Mar. 10, 2008.
Restriction Requirement from U.S. Appl. No. 11/129,006, mailed on Nov. 12, 2008.
Restriction Requirement from U.S. Appl. No. 11/137,901, mailed on Aug. 6, 2007.
Restriction Requirement from U.S. Appl. No. 11/137,901, mailed on May 23, 2008.
Restriction Requirement from U.S. Appl. No. 11/596,092, mailed on Jan. 28, 2009.
Restriction Requirement from U.S. Appl. No. 11/884,566, mailed on Apr. 5, 2010.
Restriction Requirement mailed on Oct. 14, 2010, for U.S. Appl. No. 12/732,124, filed Mar. 25, 2010, 9 pages.
Restriction Requirement mailed on Dec. 1, 2011, for U.S. Appl. No. 13/163,597, filed Jun. 17, 2011, 7 pages.
Restriction Requirement mailed on Jun. 7, 2012, for U.S. Appl. No. 13/399,828, filed Feb. 17, 2012, 5 pages.
Restriction Requirement mailed on Jul. 17, 2012, for U.S. Appl. No. 13/247,962, filed Sep. 28, 2011, 27 pages.
Restriction Requirement mailed on Sep. 11, 2012, for U.S. Appl. No. 13/399,828, filed Feb. 17, 2012, 7 pages.
Reyes et al., J. Clin. Invest. (2002) 109:337-346.
Rickert et al., Trends Cell Biol. (2000) 10:466-473.
Riesterer, Int'l J Radiation Oncology Biology Physics (2004) 361-368.
Roberts et al., Immunity (1999) 10:183-196.
Rodrigues et al., Mol. Cell. Biol. (2000) 20:1448-1459.
Rodriguez-Viciana et al., EMBO J. (1996) 15:2442-2451.
Roth et al., J. Immunol. Methods (1995) 188:97-116.
Rudd, Immunity (1996) 4:527-534.
Rupnick et al., Proc. Nat'l. Acad. Sci. (USA) (2002) 99:10730-35.
Sadhu et al., J. Immunol. (2003) 170:2647-2654.
Salven et al., Blood (1999) 94:3334-3339.
Salvesen et al., Cell (1997) 91:443-446.
Sasaki et al., Science (2000) 287:1040-1046.
Sauder et al., J. Am. Acad. Dermatol. (2002) 47:535-541.
Schimmer et al., J. Immunol. (1998) 160:1466-1471.
Schuch et al., Blood (2002) 100:4622-4628.
Schueneman et al., Canc. Res. (2003) 63:4009-4016.

Second Preliminary Amendment and Response to Notice to File Missing Parts of Nonprovisional Application from U.S. Appl. No. 12/575,277, filed Jan. 20, 2010.
Second Preliminary Amendment and Response to Notice to File Missing Parts of Nonprovisional Application from U.S. Appl. No. 12/575,367, filed Jan. 20, 2010.
Second Preliminary Amendment from U.S. Appl. No. 11/110,204, filed Aug. 24, 2007.
Second Preliminary Amendment from U.S. Appl. No. 11/884,566, filed May 13, 2008.
Sengupta et al., Circulation (2003) 107:2955-2961.
Shimamoto et al., Leukemia Res. (2003) 27:783-788.
Shiojima et al., Circ. Res. (2002) 90:1243-1250.
Shvidel et al., Hematol. J. (2002) 3:32-37.
Smith et al., Am. J. Respir. Cell Mol. Biol. (1996) 15(6):693-702.
Song et al., Canc. Res. (1974) 34:2344-2350.
Springer, Cell (1994) 76:301-314.
Stein et al., Mol. Med. Today (2000) 6:347-357.
Stenmark et al., J. Cell. Sci. (1999) 112:4175-4183.
Stennicke et al., Biochim. Biophys. Acta. (2000) 1477:299-306.
Stephens et al., Current Biology (1994) 4:203-214.
Stirewalt et al., Nat. Rev. Cancer (2003) 3:650-665.
Stoyanov et al., Science (1995) 269:690-693.
Su et al., Cancer Research (2003) 63:3585-3592.
Sumariwalla et al., Arthritis Res. Ther. (2002) 5:R32-R39.
Sunil et al., Respir. Res. (2002) 3:21.
Supplemental Amendment from U.S. Appl. No. 11/110,204, filed Oct. 27, 2009.
Supplemental Notice of Allowance from U.S. Appl. No. 10/337,192, mailed on Jun. 29, 2004.
Tager et al., J. Exp. Med. (2000) 192:439-446.
Talento et al., Transplantation (1993) 55:418-422.
Tamiya et al., Immunopharmacology (1995) 29:53-63.
Tan et al., Cancer Research (2003) 63:7663-7667.
Tan et al., J. Immunol. Meths. (2000), 238:59-68.
Tan, J. et al. (Sep. 1, 2004). "A Specific Antagonist of the p110-Delta Catalytic Component of PI3 Kinase, IC486068, Enhances Radiation-Induced Tumor Vascular Destruction," *International Journal of Radiation: Oncology Biology Physics* 60(1):S195.
Tanaka et al., J. Immunol. (1993) 151:5088-5095.
Tang et al., J. Biol. Chem. (1999) 274:16741-16746.
Taylor et al., Curr. Opin. Rheumatol. (2005) 17(3):293-298.
Tesar et al., Med. Sc. Monit. (2002) 8:BR24-BR29.
The Merck Manual on "arthritis" (2008).
The Merck Manual on "rheumatoid arthritis" (2008).
The Merck Manual, 17th ed, (1999) p. 1001.
Thelan et al., Proc. Natl. Acad. Sci. (USA) (1994) 91:4960-4964.
Ting et al., Int. J. Rad. Biol. (1991) 60:335-339.
Vacca et al., Blood (1999) 9:3064-3073.
Van Dijk et al., Blood (2000) 96:3406-3413.
Vanhaesebroeck et al., FASEB J. (1996) 10:A1395, Abst. no. 2280.
Vanhaesebroeck et al., Proc. Natl. Acad. Sci., (USA) (1997) 94:4330-4335.
Vanhaesebroeck et al., TIBS (1997) 22:267-272.
Vermes et al., J. Immunol. Meth. (1995) 184:39-51.
Vippagunta, S.R. et al. (2001). "Crystalline Solids," *Advanced Drug Delivery* 48:3-26.
Vivanco et al., Nat. Rev. Cancer (2002) 2:489-501.
Vlahos et al., J. Immunol. (1995) 154:2413-2422.
Volinia et al., Embo J. (1995) 14:3339-3348.
Volinia et al., Genomics (1994) 24:472-477.
Volinia et al., Oncogene (1992) 7:789-793.
Webb, H.K. et al. (Apr. 2009). "CAL-101, a Potent and Selective Inhibitor of the Class 1 Phosphatidylinositol 3 Kinase (PI3K) p110δ: Preclinical Summary," *Proceedings of the American Association for Cancer Research* 50:894-895, Abstract No. #3703.
Wegner et al., Lung (1992) 170:267-279.
Wegner et al., Science (1990) 247:456-459.
Weiner et al., Nat. Cell Biol. (1999) 1:75-81.
Weyand et al., Arthritis & Rheumatism (2000) 43:1041-1048.
Williams, D.A. et al. (2002). *Foye's Principles of Medicinal Chemistry*, Lippincott, Williams & Wilkins, Baltimore MD, Fifth Edition, pp. 50 and 59-61.
Williams, Methods Mol. Med. (2004) 98:207-216.
Williams et al., Chem. Biol. (2010) 17:123-134.
Wolff, ed., Burger's Medicinal Chemistry and Drug Discovery, 5th edition (1996) vol. 1, New York: John Wiley & Sons, pp. 975-977.
Wymann et al., Biochem. Biophys. Acta. (1998) 1436:127-150.
Wymann et al., Biochem. J. (1994) 298:517-520.
Wymann et al., Trends Immunol. Today (2000) 21:260-264.
Xing et al., Am. J. Pathol. (1993) 143:1009-1015.
Xu et al., Blood (2003) 102:972-980.
Yamasawa et al., Inflammation (1999) 23:263-274.
Yamaura et al., Int. J. Rad. Biol. (1976) 30:179-187.
Yao et al., Science (1995) 267:2003-2006.
Yum et al., J. Immunol. (2001) 167:6601-6608.
Zeng et al., Transplantation (1994) 58:681-689.
Zhao et al., Leukemia (2004) 18:267-75.

* cited by examiner

METHODS OF TREATMENT FOR SOLID TUMORS

CROSS-REFERENCE TO RELATED APPLICATIONS

This application claims priority from U.S. provisional application No. 61/171,047 filed Apr. 20, 2009, the contents of which are incorporated herein by reference in its entirety.

TECHNICAL FIELD

The invention is in the field of therapeutics and medicinal chemistry. In particular, the invention concerns methods of treatment for certain solid tumors that include administration of certain quinazolinone derivatives.

BACKGROUND ART

Cell signaling via 3'-phosphorylated phosphoinositides has been implicated in a variety of cellular processes, e.g., malignant transformation, growth factor signaling, inflammation, and immunity. The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring.

PI 3-kinase activation, is believed to be involved in a range of cellular responses including cell growth, differentiation, and apoptosis. FIG. 1 shows some cellular pathways by which PI3K (represented by p110 and p85) participates in solid tumor activation.

The initial purification and molecular cloning of PI3-kinase revealed that it was a heterodimer consisting of p85 and p110 subunits. Four distinct Class I PI3Ks have been identified, designated PI3K α, β, δ, and γ, each consisting of a distinct p110 catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. The patterns of expression of each of these PI3Ks in human cells and tissues are also distinct.

Identification of the p110δ isoform of PI 3-kinase is described in Chantry et al., *J. Biol. Chem.*, 272:19236-41 (1997). It was observed that the human p110δ isoform is expressed in a tissue-restricted fashion. It is expressed at high levels in lymphocytes and lymphoid tissues, suggesting that the protein might play a role in PI3-kinase-mediated signaling in the immune system. The p110β isoform of PI3K may also play a role in PI3K-mediated signaling in certain cancers. FIG. 2 illustrates the relative amounts of these isoforms of p110 in a number of different cancer cell lines. Some solid tumors exhibit little or no p110α, and many have low levels of p110δ, but all of the ones tested showed significant levels of p110β.

There is a need for a treatment of PI3K-mediated disorders relating to cancers, inflammatory diseases, and autoimmune diseases. Quinazolinone compounds have been described as generally useful for treating mainly hematologic cancers that express relatively high levels of p110δ, because the quinazolinones are more active as inhibitors of p110δ. Other PI3K inhibitors are under development for treatment of solid tumors, but they appear to be non-selective inhibitors of several isoforms of p110, or inhibitors mainly of p110α. For example, XL-147 inhibits p110α and p110δ and p110γ with similar IC-50's according to Exelixis, and has 10× lower activity on p110β; BEZ235 is described as a pan-PI3K inhibitor that also acts on mTOR; and GDC-0941 is described as a p110α inhibitor. Inhibitors with lower selectivity, or with higher levels of p110α activity, could be expected to have off-target activities; p110α, for example, is involved in regulation of glucose and insulin levels. The present invention provides a specific isomer of one quinazolinone compound that is particularly useful for the treatment of solid tumors. While it is more active on p110δ than other isoforms of PI3K, this compound's ability to treat solid tumors is believed to be due to its relatively high activity as an inhibitor of p110β combined with a high level of oral bioavailability, and it exhibits relatively low levels of functional activity against p110α.

SUMMARY

The invention provides novel methods to treat certain solid tumors, using a compound of formula (I). In one aspect, the invention provides a method of treating cancer in a subject comprising administering to said subject an optically active compound of formula I:

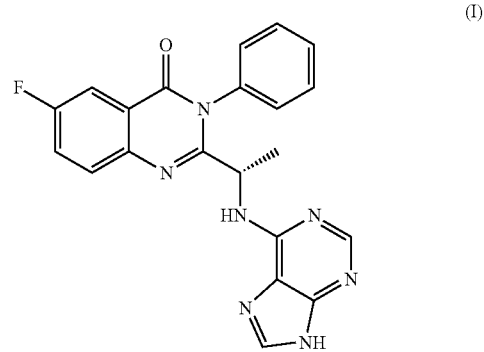 [SMILES: C[C@H](Nc1ncnc2[nH]cnc12)c1nc2ccc(F)cc2c(=O)n1-c1ccccc1]

(I)

or a pharmaceutically acceptable salt thereof. The optically active compound is predominantly the S-isomer shown here, though it may contain as a minor component some proportion of the R enantiomer. Preferably the compound used in the methods of the invention consists primarily of the S-isomer as further discussed herein.

The methods of the invention include delivery of this compound by various routes of administration, but preferably the compound is administered orally.

The subject can be any mammal; in preferred embodiments the subject is a human.

Without being bound by theory, the antitumor activity of this compound is believed to arise from its inhibition of p110β more than from inhibition of p110δ or p110α. It exhibited activity in a variety of cancer cell lines that expressed little p110δ, and some that did not express significant amounts of p110α; but all of the tested cell lines expressed p110β.

Moreover, compound I exhibited comparatively low functional activity on p110α in a cell-transformation system designed to measure functional activity of these kinases, but is a potent inhibitor of both p110β and p110δ in that assay. See Example 1. This chick embryo fibroblast (CEF) transformation system has been reported as a useful way to assess the functional activity of the PI3K signaling pathway. Denley, et al., "*Oncogenic signaling of class I PI3K isoforms,*" *Oncogene*, vol. 27(18), 2561-74 (2008). Transformation of CEF cells in the assay depends upon functional kinase activity. Kang, et al., *Proc. Nat'l Acad. Sci. USA*, vol. 103(5), 1289-94 (2006). Similarly in other functional cell-based assays, Compound I is most active on p110δ and p110β, with relatively lower activity against p110α.

As FIG. 4 illustrates, Compound I at 10 micromolar inhibits phosphorylation of Akt, which is a downstream mediator of PI3K activation (See FIG. 1), in two cancer cell lines, T47D (breast cancer) and OVCAR-3 (ovarian cancer). It is significant, too, that T47D has a mutation that activates p110α, yet that does not significantly reduce the effect of Compound I against this cell line, further suggesting that the antitumor activity of this compound must reside in its effect on other isoforms rather than on p110α. This distinguishes compound I from other known PI3K inhibitors in development for treatment of solid tumors, which are believed to act primarily at the p110α isoform or on p110α plus other isoforms, or even on all PI3Ks plus mTOR.

Compound I is useful to treat certain cancers. In some embodiments the cancer is a non-hematopoietic cancer. In some embodiments, the cancer is a solid tumor selected from pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; melanoma; neuroendocrine cancers; CNS cancers; brain tumors; bone cancer; and soft tissue sarcoma. In some embodiments it is lung cancer (non-small cell lung cancer, small-cell lung cancer), colon cancer, CNS cancer, melanoma, ovarian cancer, renal cancer, prostate cancer or breast cancer.

In some embodiments, the method comprises administering an effective amount of compound I or a pharmaceutically acceptable salt of compound I, to a subject afflicted with one of these cancers. In preferred embodiments, the compound is administered orally. The compound may be administered alone or in the form of a pharmaceutical composition that comprises compound I admixed with at least one pharmaceutically acceptable excipient.

In particular embodiments, the cancer is breast cancer, lung cancer, prostate cancer, renal cancer, or ovarian cancer. In a particular embodiment, the method comprises administering to the subject to be treated, in addition to a compound of formula I, a therapeutically effective amount of at least one additional therapeutic agent and/or an additional therapeutic procedure selected to treat the cancer.

The invention thus provides a method of treating a solid tumor in a subject comprising administering to said subject an optically active compound of formula I or a pharmaceutically acceptable salt thereof, or a pharmaceutical composition comprising an optically active compound of Formula I or a pharmaceutically acceptable salt thereof, wherein the amount of the compound of Formula I or its salt is an amount effective to treat the solid tumor.

In certain embodiments, the solid tumor is selected from the group consisting of pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; melanoma; neuroendocrine cancers; CNS cancers; brain tumors; bone cancer; and soft tissue sarcoma. In some embodiments, the solid tumor is selected from non-small cell lung cancer, small-cell lung cancer, colon cancer, CNS cancer, melanoma, ovarian cancer, renal cancer, prostate cancer and breast cancer.

For methods of the invention, compound I is optically active. Preferably, the S-enantiomer predominates over the R enantiomer by a ratio of at least about 9:1. In specific embodiments, the S-enantiomer predominates over the R enantiomer by a ratio of at least about 19:1.

In preferred embodiments, Compound I is administered orally. Typically, it is administered in a solid form, and commonly it is admixed with a pharmaceutically acceptable diluent or excipient.

The method is applicable to the treatment of a variety of tumor types. In some embodiments, the cancer is ovarian, renal, breast, lung, colon or prostate cancer.

The subject is a mammal, and is typically a human. In some embodiments, the subject is refractory to chemotherapy treatment, or is in relapse after treatment with chemotherapy. The methods of the invention are also useful to reduce the level of activity of p110β in the subject.

The compound of Formula I can be administered at a dose of 20-500 mg/day. In some embodiments, the compound of formula I is administered at least twice daily. In specific embodiments, it is administered at a dose of 50-250 mg/day. In some embodiments, it is administered at a dose of 50-150 mg twice per day.

In some embodiments, the dose of Compound I is selected to provide a concentration of compound I in the blood that reaches a point between 40 and 10,000 ng/mL over a 12 hour period from the time of administration. In some embodiments, the dosing provides a concentration of compound I in the blood that is between about 100 ng/mL and 6000 ng/mL in the treated subject. In some embodiments, dosing is selected to produce a Cmax (peak plasma level) of Compound I between 1000 ng/mL and 8,000 ng/mL.

Compound I can be administered orally, transdermally, or by injection or inhalation. In some embodiments, it is administered orally.

In another aspect, the invention provides a combination therapy for treating cancer, comprising administering Compound I to a subject who is concurrently receiving treatment with an additional therapeutic agent, or an additional cancer therapy.

In some embodiments, the additional therapeutic agent to be used along with Compound I is selected from the following group consisting of Docetaxel, Mitoxantrone, Prednisone, Estramustine, Anthracyclines, (doxorubicin (Adriamycin), epirubicin (Ellence), and liposomal doxorubicin (Doxil)), Taxanes (docetaxel (Taxotere), paclitaxel (Taxol), and protein-bound paclitaxel (Abraxane)), Cyclophosphamide (Cytoxan), Capecitabine (Xeloda) and 5 fluorouracil (5 FU), Gemcitabine (Gemzar), methotrexate, Vinorelbine (Navelbine), an EGFR inhibitor such as erlotinib, Trastuzumab, Herceptin, Avastin, Platins (cisplatin, carboplatin), Temazolamide, Interferon alpha, and IL-2. In some embodiments, it is selected from the group consisting of an EGFR inhibitor, an mTOR inhibitor, a platin, and a taxane.

In some embodiments, the therapeutic procedure to be used along with Compound I is selected from the group consisting of peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, immunohistochemistry staining method, pharmacological study, low-LET cobalt-60 gamma ray therapy, bleomycin, conventional surgery, radiation therapy, high-dose chemotherapy and nonmyeloablative allogeneic hematopoietic stem cell transplantation.

In some embodiments, the methods of the invention further comprise obtaining a biological sample from said subject;

and analyzing the biological sample with an analytical procedure selected from the group consisting of blood chemistry analysis, chromosomal translocation analysis, needle biopsy, fluorescence in situ hybridization, laboratory biomarker analysis, immunohistochemistry staining method, flow'cytometry or a combination thereof. Analysis provides information that can be used to determine whether to adjust the dose of Compound I up or down, or to terminate treatment with Compound I, or to add an additional therapeutic agent or therapeutic procedure to the treatment methods using Compound I.

In some embodiments, Compound I is administered twice daily for about 28 days, and is then discontinued for at least 7 days.

The following detailed description is to aid in understanding and employing the methods of the invention.

MODES OF CARRYING OUT THE INVENTION

Figure 1:
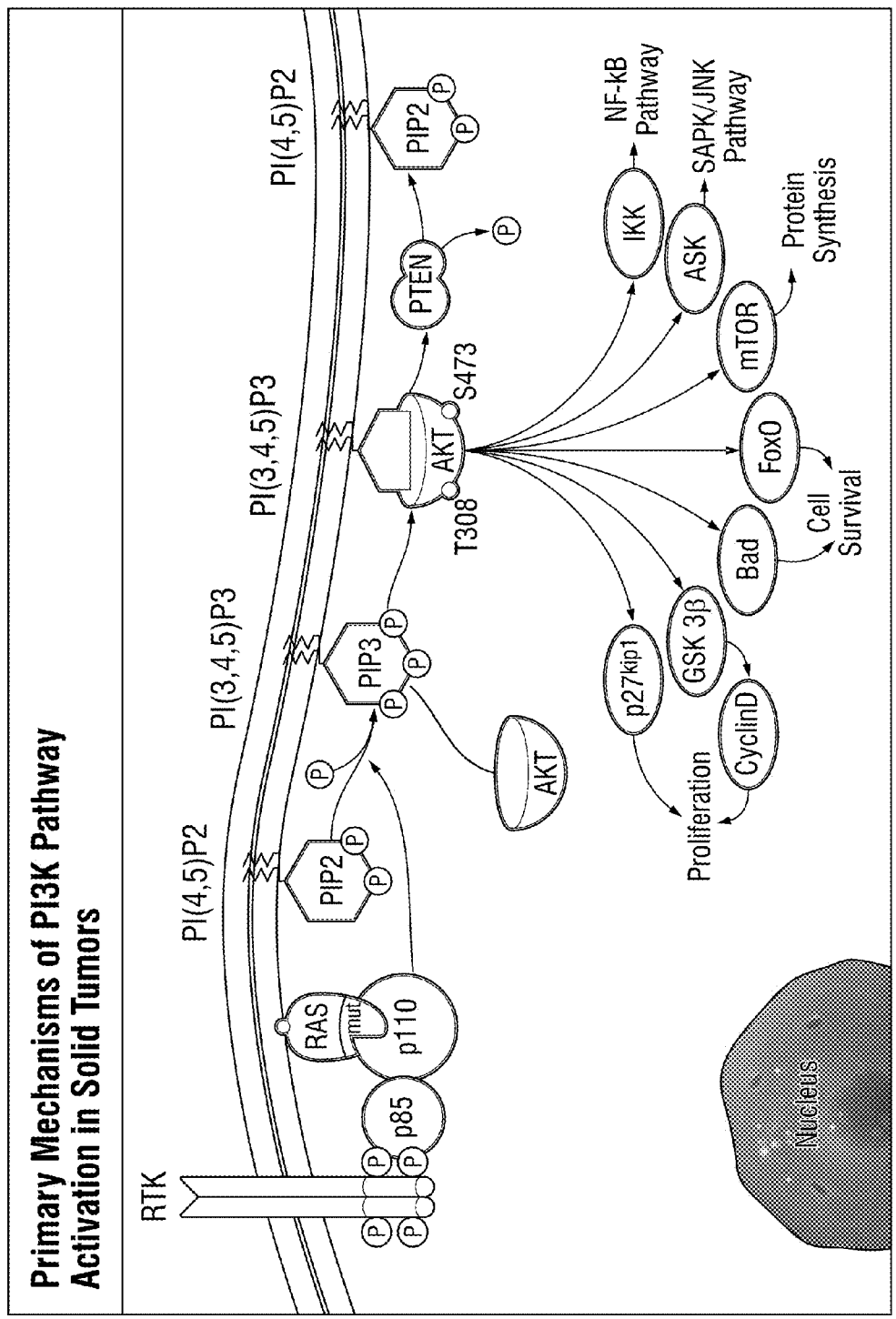
FIG. 1 shows part of the PI3K signaling pathway associated with solid tumor activation.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

The discussion of the general methods given herein is intended for illustrative purposes only. Other alternative methods and embodiments will be apparent to those of skill in the art upon review of this disclosure.

A group of items linked with the conjunction "or" should not be read as requiring mutual exclusivity among that group, but rather should also be read as "and/or" unless expressly stated otherwise. Although items, elements, or components of the invention may be described or claimed in the singular, the plural is contemplated to be within the scope thereof unless limitation to the singular is explicitly stated.

The invention provides methods that relate to a novel therapeutic method for the treatment of cancer and particularly solid tumors. The invention comprises administering to said subject a compound of formula I:

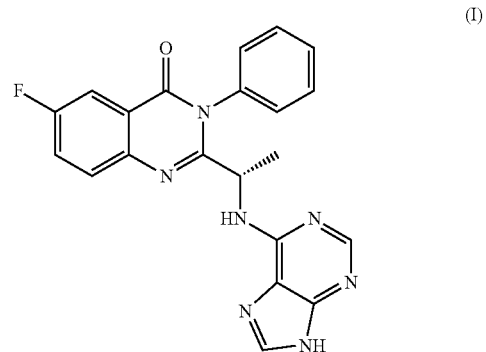 [SMILES: C[C@H](Nc1ncnc2[nH]cnc12)c1nc2ccc(F)cc2c(=O)n1-c1ccccc1]

or a pharmaceutically acceptable salt thereof, or a pharmaceutical composition comprising a compound of formula (I) or a pharmaceutically acceptable salt thereof, optionally admixed with at least one pharmaceutically acceptable excipient.

Compound I for use in the methods described herein is optically active, meaning it consists of predominantly one of two enantiomers. The compound has a single chiral center, in the noncyclic linking group between the quinazolinone moiety and the purine moiety. The chiral center of the preferred enantiomer of the compound of Formula (I) is the S-isomer depicted above. The compound is used in optically active form, which contains predominantly the S-enantiomer. This compound may be synthesized in optically active form, or it may be prepared in racemic form (containing equal amounts of R and S isomers), and then the isomers may be separated. A chiral synthesis of Compound I that provides the S enantiomer in very high optical purity is depicted herein. See FIG. 5. While it is preferable to substantially exclude the enantiomeric R isomer from the compound of Formula (I) for purposes of the invention, the methods can be practiced with mixtures of R and S isomers, provided the S isomer is the major component of the mixture. Typically such mixture will contain no more than about 10% of the R isomer, meaning the ratio of S to R isomers is at least about 9:1, and preferably less than 5% of the R-isomer, meaning the ratio of S to R enantiomers is at least about 19:1. In some embodiments the compound used has less than 2% R enantiomer, meaning it has an enantiomeric excess of at least about 96%.

The methods of the invention utilize an optically active form of Compound I (the compound of Formula I), meaning in each instance, the compound is optically active and contains predominantly the S-enantiomer, although it may contain the R-enantiomer of Compound I as a minor component. For clarity, where a dosage of a compound of Formula I, or a dosage of Compound I is described herein, the dosage refers to the weight of the compound of Formula I, including each enantiomer that is present. Thus a dosage of 100 mg of Compound I as used herein, for example, refers to the weight of the mixture of enantiomers rather than the weight of the S-enantiomer specifically. It could, for example, refer to 100 mg of a 9:1 mixture of S and R enantiomers, which would contain about 90 mg of the S enantiomer, or to 100 mg of a 19:1 mixture of S and R enantiomers, which would contain about 95 mg of the S enantiomer.

The methods of the invention are useful to treat cancers, particularly solid tumors. In some embodiments, the cancer is a solid tumor selected from pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; melanoma; neuroendocrine cancers; CNS cancers; brain tumors; bone cancer; and soft tissue sarcoma. In some embodiments it is lung cancer (non-small cell lung cancer, small-cell lung cancer), colon cancer, CNS cancer, melanoma, ovarian cancer, renal cancer, prostate cancer or breast cancer.

The efficacy of compound I is believed to arise from its in vivo inhibition of p110β activity primarily, though it also inhibits p110δ activity. Compound I is selective for inhibition of p110β and p110δ over p110α, and is selective for these two kinases over other kinases against which it has been tested. Its selectivity is illustrated by its activity in a cellular assay of functional activity, where it inhibited p110β with an EC-50 of about 150 nM, and p110δ with an EC-50 of about 15 nM, while showing much less activity on p110α (EC-50 was above 2000 nM). Even though its activity against p110β is lower than its activity on p110δ, because p110β is the dominant isoform of p110 that is observed in solid tumors, it is believed that the activity on the delta isoform is less important to its solid tumor activity than its activity on p110β. This is also consistent with the observation that Compound I exhibits activity against tumors that express little or no p110δ (suggesting they do not rely on it), and against tumor cell lines where p110α is activated (see T47D discussion above), suggesting that high levels of the alpha isoform do not reduce sensitivity to Compound I.

Selectivity with respect to p110α is important to the safety profile of Compound I: p110α plays an essential role in insulin signaling and glucose metabolism. Nonselective PI3K inhibitors that also inhibit p110α activity are expected to cause side effects or off-target adverse effects by affecting insulin signaling and/or glucose metabolism, which do not seem to occur with Compound I. This is believed to contribute to reduction of off-target effects for Compound I.

Compound I is also selective for these PI3K isoforms over other lipid kinases, including other PI3K kinases, DNA-PK (another serine-threonine kinase), and mTOR. This table provides IC-50's for inhibition of kinase activity of these other lipid kinases:

| PIKC3 | 2500 nM |
| DNA-PK | 13,000 nM |
| mTOR | 100,000 nM |

Moreover, compound I has comparatively low activity on p110α in a cell-transformation system designed to measure functional activity of these kinases, but is a potent inhibitor of both p110β and p110δ in that assay. See Example 1. This chick embryo fibroblast (CEF) transformation system has been reported as a useful way to assess the functional activity of the PI3K signaling pathway. Denley, et al., "*Oncogenic signaling of class I PI3K isoforms,*" *Oncogene*, vol. 27(18), 2561-74 (2008). Transformation of CEF cells in the assay depends upon functional kinase activity. Kang, et al., *Proc. Nat'l Acad. Sci. USA*, vol. 103(5), 1289-94 (2006). The readout of this assay is based on the frequency of transformation of CEF cells exposed to viral vectors carrying a specific p110 isoform of interest. See FIG. 3.

In this system, an EC-50 for functional activity of p110α was not reached at the highest concentration of Compound I tested (2000 nM); the EC-50 for inhibition of functional activity of p110β by Compound I was about 150 nM; and the EC-50 for inhibition of functional activity of p110δ by Compound I was about 15 nM.

Similarly, other functional assays of inhibition of specific isoforms in cell-based tests showed compound I to have higher activity on the delta and beta isoforms of p110 than on p110α. The p110α assay used SW3T3 cells stimulated by PDGF, and p110 kinase activity was measured by Akt phosphorylation. The p110β activity was measured by lysophosphatidic acid stimulation of Akt phosphorylation in mouse embryonic fibroblasts. The activity of p110δ was measured by anti-FcεR1 antibody cross linking stimulation of CD63 movement to the surface of basophils. Finally, the activity of p110γ was measured by fMLP stimulation of CD63 antigen movement to the cell surface of basophils. Again, compound I showed little inhibition of the alpha isoform, and was most active on the delta and beta isoforms.

| Cell-based assay EC$_{50}$ (nM) | p110α | >20,000 |
| --- | --- | --- |
| | p110β | 1,200 |
| | p110δ | FB/WB 8.4/19 |
| | p110γ | 3,000/5,400 |

Figure 4A:
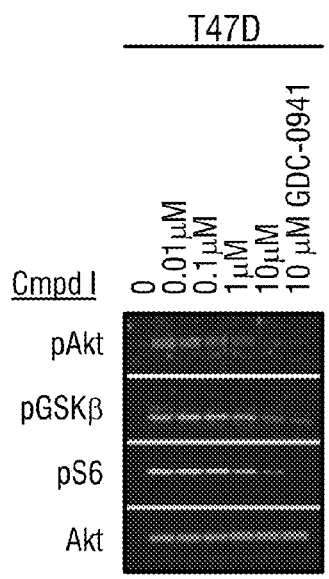
FIG. 4a-b shows how Compound I, at concentrations from 0.01 uM to 10 uM, affects phosphorylation of Akt, GSKβ, and S6 in two cancer cell lines, compared to how GDC-0941, which is described as a p110alpha inhibitor affects the same phosphorylations.
Figure 4B:
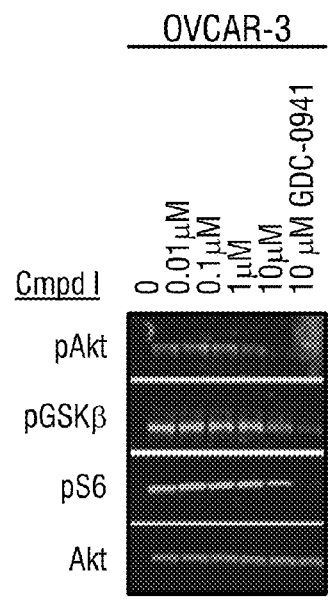

As FIG. 4 illustrates, Compound I at 10 micromolar inhibits phosphorylation of Akt, which is a downstream mediator of PI3K activation (See FIG. 1), in two cancer cell lines, T47D (breast cancer) and OVCAR-3 (ovarian cancer). It is significant to note that T47D has a mutation that activates p110α, yet compound I provides good activity against this cell line, further demonstrating that the antitumor activity of this compound most likely resides in its effect on other isoforms rather than on p110α.

Figure 6:
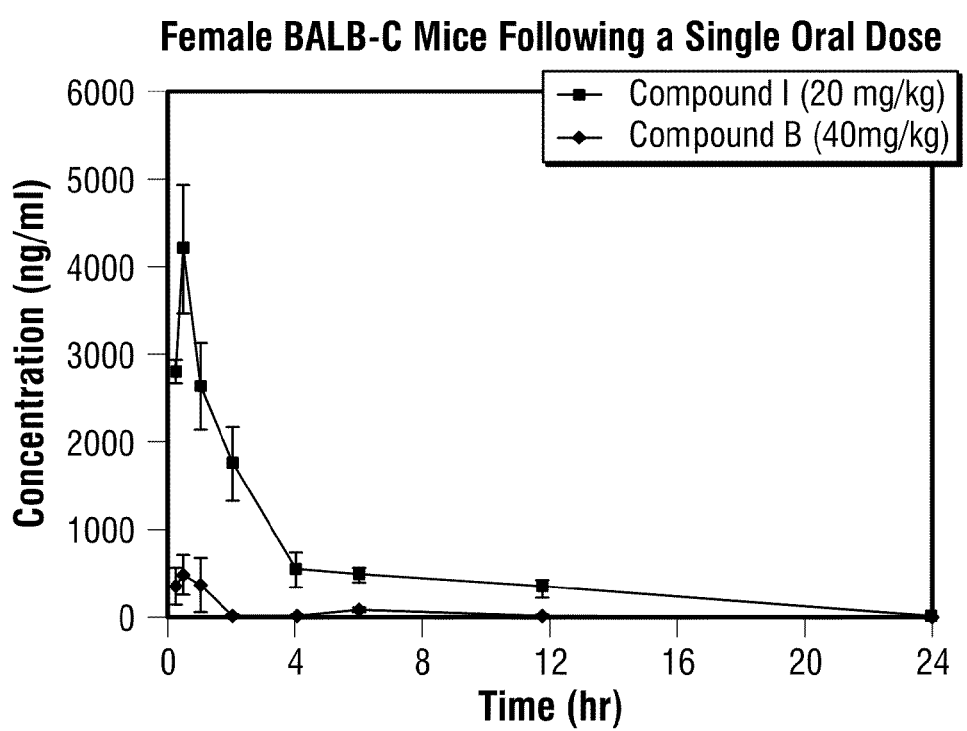
FIG. 6 shows plasma levels of Compound I in mice that received a single oral dose of the compound, compared to plasma levels of another quinazolinone compound (Compound B) with a similar structure, to illustrate the high oral bioavailability provided by Compound I.

Bioavailability of Compound I upon oral administration is especially good; even compared to other quinazolinones of similar structures. For example, FIG. 6 illustrates that Compound I produces higher plasma concentrations of drug than another quinazolinone compound having a similar structure (Compound B). Note that Compound I was administered orally to mice at half the dosage of Compounds B, but produced a higher peak plasma level. The degree of difference in oral bioavailability between Compound I and Compound B observed in this test is surprising.

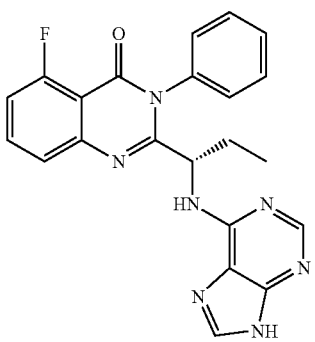

Compound B

Treatments of the invention typically involve administration of compound I to a subject in need of treatment on a daily basis for at least one week or more than one week, often for 2-4 weeks, and sometimes for 1-3 months or more. The half-life of Compound I in vivo in mice and rats is several hours—see FIG. 6. It is thus sometimes desirable to administer compound I in multiple doses each day, in order to maintain efficacious plasma levels over a prolonged period of time. Administration may be done in two doses per day, or three doses per day, or in some embodiments, four doses per day or more, particularly when Compound I is administered orally. Alternatively, Compound I can be administered intravenously at a rate that maintains an efficacious plasma level for a prolonged period of time. Suitably, it would be administered at a rate to achieve a plasma level of at least about 1 micromolar, or at least 3 micromolar, or at least 5 micromolar. FIG. 6 shows that plasma levels of about 500 ng/mL (over 1 micromolar) can be maintained for several hours following a single oral dose of 20 mg/kg of Compound I; this demonstrates that high plasma levels of Compound I, e.g., concentrations consistent with the levels shown to be effective in functional assays, can be achieved with tolerated doses of compound I.

Figure 7A:
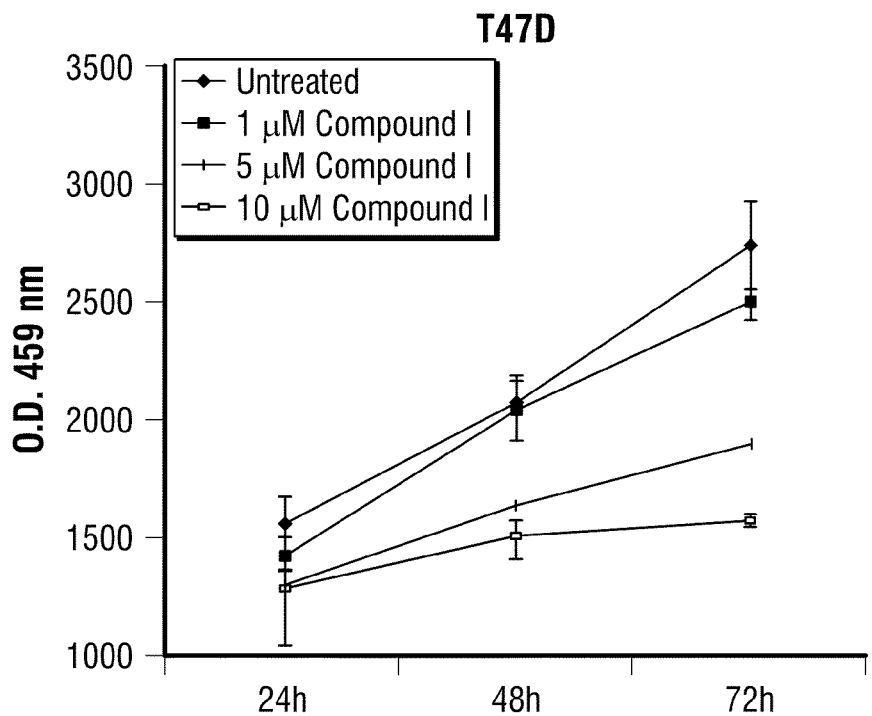
FIG. 7a-b shows dose-dependent inhibition of growth of tumor cell cultures for two different tumor lines.
Figure 7B:
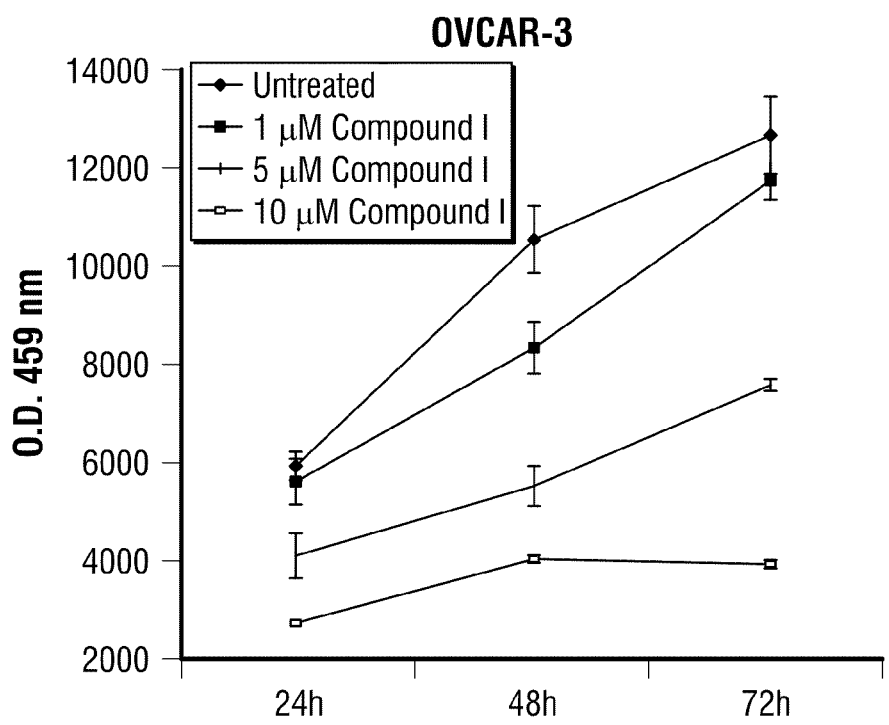

Compound I has been shown to induce apoptosis of a variety of solid tumor cells. FIG. 7 shows its dose-dependent inhibition of tumor cell culture growth, measured by optical density at 459 nm, for a breast cancer cell line (T47D) and an ovarian cancer cell line (OVCAR-3). It demonstrates that exposure to 5-10 micromolar levels of Compound I provides strong inhibition of growth in cell cultures.

Figure 8:
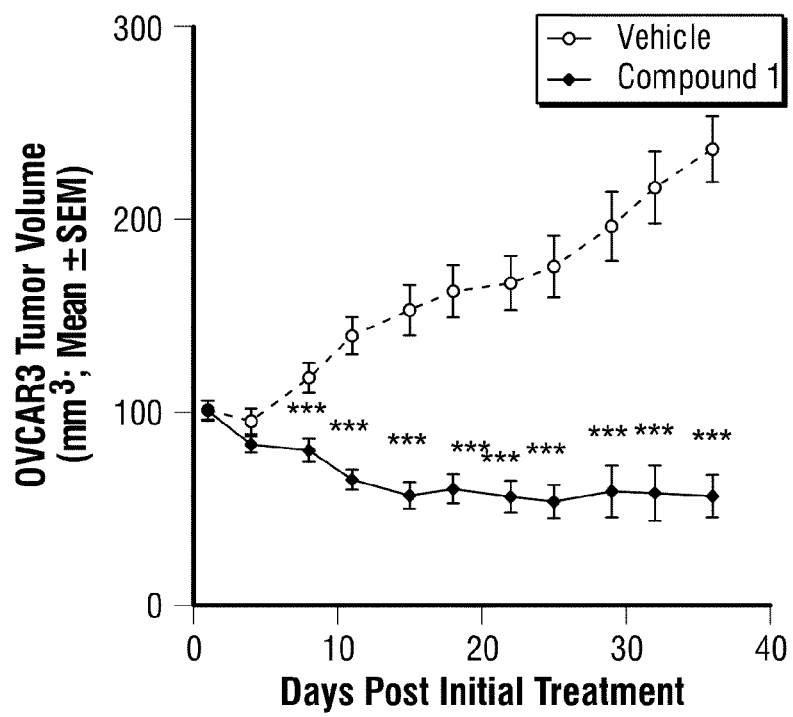
FIG. 8 shows that Compound I at 30 mg/kg BID completely inhibited growth of a tumor xenograft over a five week period, while the corresponding xenografts in untreated control animals more than doubled in volume over the same time period.

FIG. 8 shows a dose-dependent inhibition of growth of an ovarian cancer xenograft tumor, as judged by measuring tumor volume, upon treatment with Compound I. Tumor volume actually decreased during a treatment lasting over 30 days in treated animals receiving 30 mg/kg Compound I, BID, while tumor volume more than doubled in the untreated control animals during the same time period. This demonstrates that Compound I is effective to treat a solid tumor in vivo.

Figure 9:
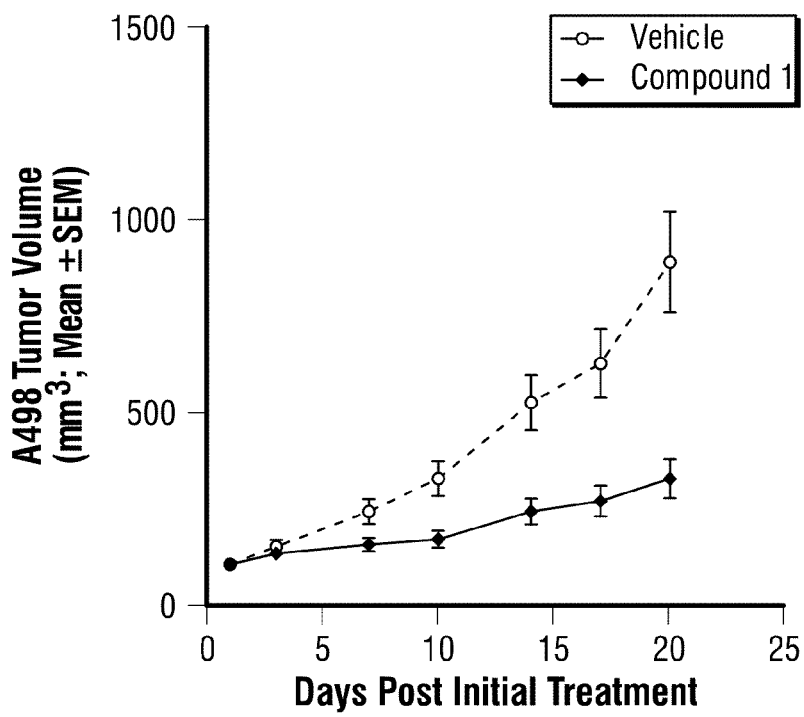
FIG. 9 shows that Compound I at 30 mg/kg BID significantly inhibited growth of a tumor xenograft over a three week period, while the corresponding xenografts in untreated control animals expanded much more rapidly during the same time period.

Similarly, FIG. 9 shows efficacy of Compound I for treating another solid tumor xenograft (A498, a human renal cancer cell line). As the Figure shows, treatment of mice bearing A498 tumors with Compound I at 30 mg/kg BID for 20 days produced effective antitumor activity in vivo. While tumor volume approximately doubled over this time in the treated animals, it increased more than 5-fold in the untreated animals. Again, this shows compound I is effective to treat a solid tumor in vivo.

Figure 10:
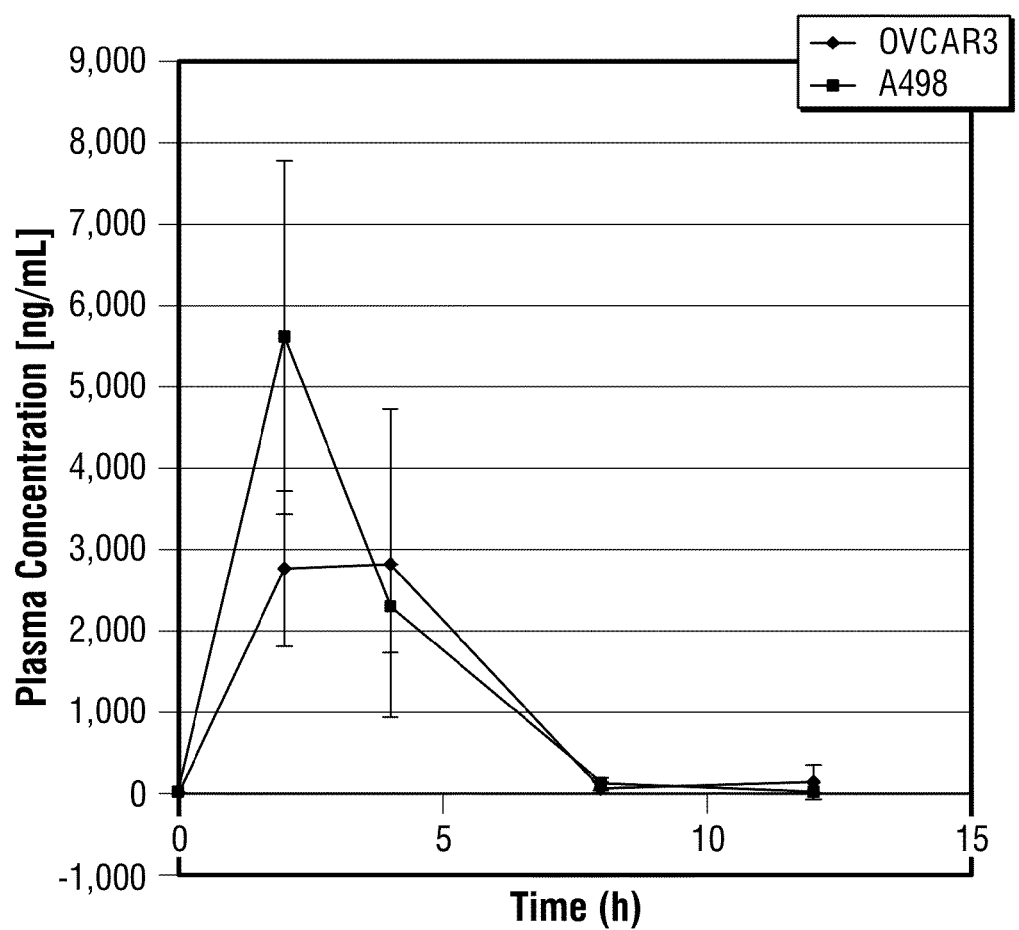
FIG. 10 shows the plasma concentration profile for Compound I in the xenograft-bearing mice of FIGS. 8 and 9, when administered as a single dose of 30 mg/kg.

FIG. 10 shows plasma concentrations of Compound I in the mice bearing each of the tumor xenografts used for FIGS. 8 and 9, following a single oral dose of Compound I at 30 mg/kg. At this range, which was the effective dosage used in the tests shown in FIGS. 8 and 9, plasma concentration of compound I reaches about 5000-7000 ng/mL.

Figure 11:
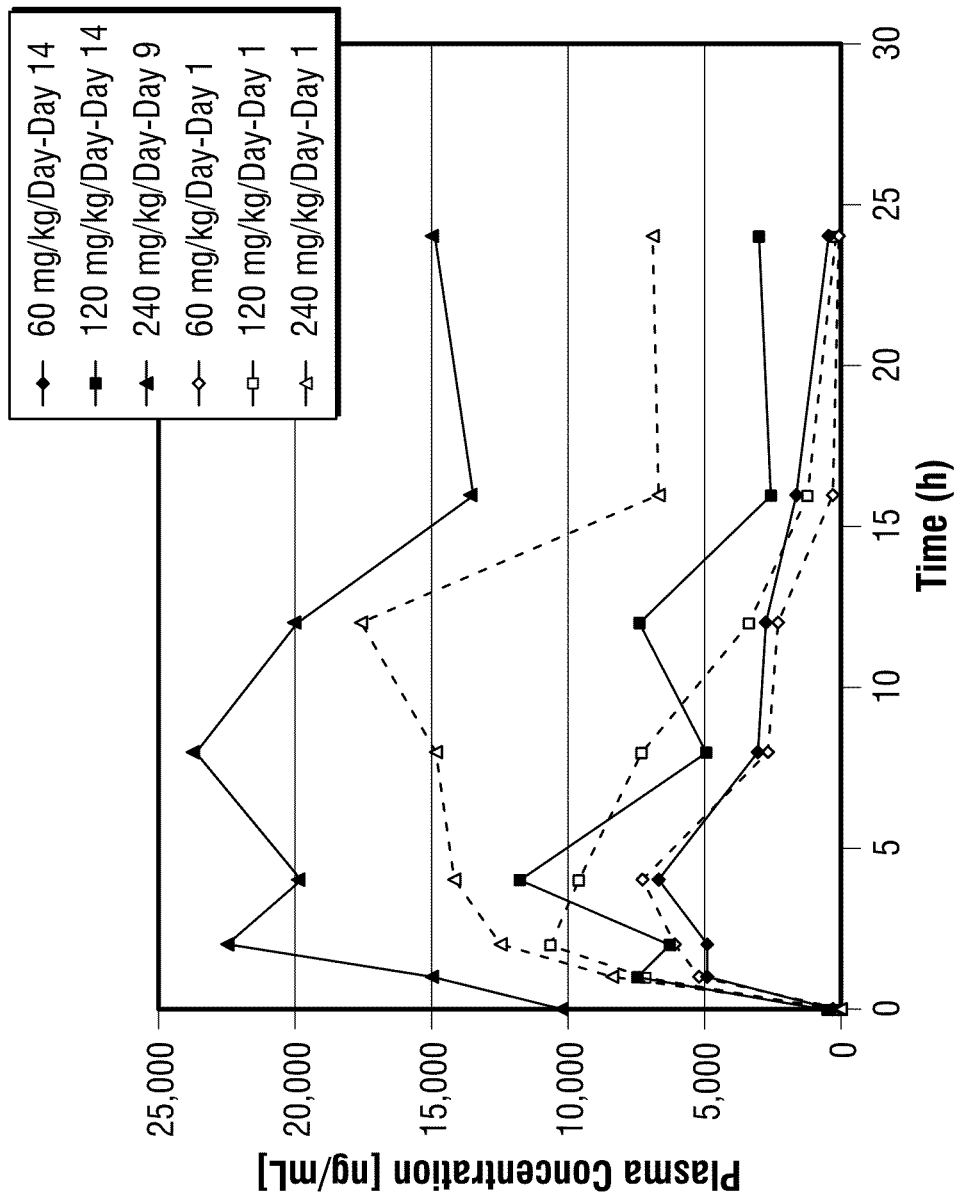
FIG. 11 shows the plasma concentration profiles on the first and last days of multi-day testing of compound I in healthy mice receiving 60 mg/kg, 120 mg/kg, or 240 mg/kg per day. The 60 mg/kg dose was well tolerated, demonstrating that the treatment dose (30 mg/kg BID) is both tolerated and effective in mice.

FIG. 11 shows the plasma concentration profiles on the first and last days of multi-day testing of compound I in healthy mice receiving 60 mg/kg, 120 mg/kg, or 240 mg/kg per day. The 60 mg/kg dose was well tolerated, demonstrating that the treatment dose (30 mg/kg BID) is both tolerated and effective in mice.

Compound I has also been tested in a battery of tumor cell assays known as the NCI panel. It demonstrated substantial growth inhibition of most of the cancer cell lines in the panel, and was generally more active on these cancer cell lines than Compound B, which was included for comparison. The following Table shows the GI-50 (concentration providing 50% growth inhibition, in μM) for each compound in these cell culture assays.

| Tumor Type | Cell Line | Compound B GI-50 (μM) | Compound I GI-50 (μM) |
|---|---|---|---|
| Non-Small Cell Lung Cancer | A549 | 50.4 | 20.7 |
| | EKVX | 28.2 | 16.7 |
| | HOP-62 | 39.7 | 14.8 |
| | HOP-92 | 34.8 | 0.3 |
| | NCI-H226 | 100 | 100 |
| | NCI-H23 | 100 | 100 |
| | NCI-H322M | 32.2 | 10.5 |
| | NCI-H460 | 34.7 | 25.7 |
| | NCI-H522 | 52.7 | 51.8 |
| Colon Cancer | COLO 205 | 30.1 | 33.8 |
| | HCC-2998 | 53.3 | 32.4 |
| | HCT-116 | 54.3 | 37.9 |
| | HCT-15 | 48.4 | 30.3 |
| | HT29 | 39.1 | 16.5 |
| | KM12 | 54.1 | 2 |
| | SW-620 | 86.4 | 69.3 |
| CNS Cancer | SF-268 | 29.8 | 1.89 |
| | SF-295 | 8.18 | 1.81 |
| | SF-539 | 28.6 | 15.9 |
| | SNB-19 | 54.8 | 19.3 |
| | SNB-75 | 2.96 | 0.0594 |
| | U251 | 70.4 | 59.6 |
| Melanoma | LOX IMVI | 31.1 | 36.1 |
| | MALME-3M | 31.6 | 4.58 |
| | M14 | 58.4 | 88.9 |
| | SK-MEL-2 | 100 | 100 |
| | SK-MEL-28 | 38.6 | 12.8 |
| | SK-MEL-5 | 32.9 | 31.3 |
| | UACC-257 | 33.5 | 17.4 |
| | UACC-62 | 4.2 | 1.43 |
| Ovarian | IGROV1 | 3.54 | 2.7 |
| | OVCAR-3 | 15.5 | 0.316 |
| | OVCAR-4 | 100 | 100 |
| | OVCAR-5 | 40.1 | 27.7 |
| | OVCAR-8 | 96 | 44.6 |
| | SK-OV-3 | 13.8 | 4.02 |
| Renal | 786-0 | 5.48 | 1.99 |
| | A498 | 2.38 | 0.615 |
| | ACHN | 24.4 | 10.7 |
| | CAKI-1 | 13.4 | 1.01 |
| | RXF 393 | 74.2 | 1.14 |
| | SN12C | 11 | 22.5 |
| | TK-10 | 31.7 | 1.24 |
| | UO-31 | 5.32 | 2.01 |
| Prostate | PC-3 | 12 | 0.647 |
| | DU-145 | 43.8 | 1.35 |
| Breast Cancer | MCF7 | 7.08 | 2.54 |
| | ADR-RES | 77.9 | 58.6 |
| | MDA-MB-231 | 100 | 100 |
| | HS 578T | 6.91 | 2.24 |
| | MDA-MB-435 | 16.4 | 43.1 |
| | BT-549 | 14.3 | 0.538 |
| | T-47D | 3.18 | 0.571 |
| | MDA-MB-468 | 13.6 | |

As a means of comparing the overall activity of these two compounds on diverse solid tumor cell types, the numbers of cell lines that have GI50 values of 2 micromolar or less were determined for each compound; these cell lines were considered particularly sensitive ones. Using this measure, 1.8% of cell lines were particularly sensitive to Compound B at this level, while 39% were particularly sensitive to Compound I at the same concentration. Despite structural similarity to Compound B, it is apparent that Compound I is much more active on solid tumors than compound B.

Below is a table of the number of cell lines for each type of tumor that were found to have GI50 values less than 2 micromolar for Compound I.

| Tumor Type | Cell line number | % $EC_{50}$ < 2 µM |
|---|---|---|
| NSCLC | 1/9 | 11% |
| Colon | 1/7 | 14% |
| CNS | 3/6 | 50% |
| Melanoma | 1/8 | 12% |
| Ovarian | 2/6 | 33% |
| Prostate | 2/2 | 100% |
| Renal | 6/8 | 75% |
| Breast | 5/8 | 62% |

In a particular embodiment, the cancer is a solid tumor such as lung cancer (non-small cell lung cancer, small-cell lung cancer), colon cancer, CNS cancer, melanoma, ovarian cancer, renal cancer, prostate cancer or breast cancer. As the above table indicates, breast, renal, prostate and CNS cancers are particularly sensitive to compound I, so in some embodiments, the method is used to treat a subject having any one of these cancers.

In a particular embodiment, the cancer is not a hematological cancer, e.g., it is not a lymphoma or leukemia or multiple myeloma. Exemplary solid tumors treatable by the methods disclosed herein include breast, lung, colon, ovarian, renal, and prostate cancer.

In a particular embodiment, a compound of formula I is administered in a therapeutically effective amount, to a subject diagnosed with at least one cancer disclosed as treatable by the methods herein.

The therapeutically effective amount can be determined by one of ordinary skill based on the subject's health, age, body weight, and condition. In some embodiments, the amount is normalized to the subject's body weight. For example, a dosage may be expressed as a number of milligrams of Compound I per kilogram of the subject's body weight (mg/kg). Dosages of between about 0.1 and 100 mg/kg are often appropriate, and in some embodiments a dosage of between 0.5 and 60 mg/kg is used. Normalizing according to the subject's body weight is particularly useful when adjusting dosages between subjects of widely disparate size, such as when converting an effective dosage in a dog to a dosage suitable for a human subject.

In other embodiments, the daily dosage may be described as a total amount of Compound I administered per dose or per day. Daily dosage of Compound I is typically between about 10 mg and 1000 mg. When administered orally, the total daily dosage for a human subject is typically between about 50 mg and 750 mg.

In a particular embodiment, a compound of formula I is administered at a dose of 20-500 mg/day.

In a particular embodiment, a compound of formula I is administered at a dose of 50-250 mg/day.

In a particular embodiment, a compound of formula I is administered at a dose of 25 to 150 mg per dose, and two to four doses are administered per day (e.g., BID dosing with 25 to 150 mg doses, or TID dosing with doses between 25 and 150 mg, or QID dosing with doses between 25 and 150 mg). In a preferred embodiment, a subject is treated with 50 mg to 100 mg doses of Compound I twice per day, or 50-100 mg doses three times per day, or 50-100 mg doses four times per day.

Treatment with the compounds of the invention are frequently continued for a number of days; for example, commonly treatment would continue for at least 7 days, about 14 days, or about 28 days, for one cycle of treatment. Treatment cycles are well known in cancer chemotherapy, and are frequently alternated with resting periods of 1-28 days, commonly 7 days or 14 days, between cycles.

In a particular embodiment, the method comprises administering to said subject an initial daily dose of 20-500 mg of a compound of formula I and increasing said dose by increments until clinical efficacy is achieved. Increments of about 25, 50, or 100 mg can be used to increase the dose. The dosage can be increased daily, every other day, twice per week, or once per week.

In a particular embodiment, this method comprises continuing to treat said subject by administering the compound of formula I at a dosage where clinical efficacy is achieved for a week or more, or reducing said dose by increments to a level at which efficacy can be maintained. Efficacy can be monitored by conventional methods such as assessing tumor size or spreading (metastasis).

In a particular embodiment, the method comprises administering to said subject an initial daily dose of 20-500 mg of a compound of formula I and increasing said dose to a total dosage of 50-400 mg per day over at least 6 days. Optionally, the dosage can be further increased to about 750 mg/day.

In a particular embodiment, a compound of formula I is administered at least twice daily. In some embodiments the compound is administered three times per day. In some embodiments the compound is administered four times per day, or more than four times per day.

In a particular embodiment, the method comprises reducing the level of PI3Kβ activity in the subject.

In a particular embodiment, the subject is a human subject. Typically the subject is a human diagnosed as having a cancer disclosed herein as treatable by compound I.

In a particular embodiment, the compound is administered at a rate selected to produce a concentration of compound in the blood between about 40 ng/mL and 3,000 ng/mL, and maintaining such concentration during a 4-12 hour period following administration. In another particular embodiment, the dose size and frequency are selected to achieve a concentration of compound in the blood that is between 75-2,000 ng/mL and maintain that concentration during a 4-12 hour period from the time of administration. In some embodiments, the dose size and frequency are selected to achieve a concentration of compound in the blood that is between 100-1,000 ng/mL following administration. In some embodiments, the dose size and frequency are selected to achieve a concentration of compound in the blood that is between 100-500 ng/mL over a 12 hour period from the time of administration. Desirably, the dose size and frequency are selected to achieve a $C_{max}$, plasma level of Compound I that is at least about 500 ng/mL and does not exceed about 10,000 ng/mL.

In certain embodiments, Compound I is administered orally, intravenously, transdermally, or by inhalation. Preferably, the compound is administered orally. In some embodiments, it is administered orally in a dose of about 25 mg, 30 mg, 40 mg, 50 mg, 60 mg, 75 mg, or 100 mg, 125 mg, 150 mg, or 200 mg per dose, and the dose may be administered at a frequency of once per day, twice per day, three times per day, or four times per day.

In a particular embodiment, the method comprises administering in addition to a compound of formula I to said subject a therapeutically effective amount of at least one additional therapeutic agent and/or a therapeutic procedure selected to treat said cancer or autoimmune disease in said subject.

In a particular embodiment, said therapeutic agent is selected from the following group consisting of Docetaxel, Mitoxantrone, Prednisone, Estramustine, Anthracyclines, (doxorubicin (Adriamycin), epirubicin (Ellence), and liposomal doxorubicin (Doxil)), Taxanes (docetaxel (Taxotere), paclitaxel (Taxol), and protein-bound paclitaxel (Abraxane)), Cyclophosphamide (Cytoxan), Capecitabine (Xeloda) and 5 fluorouracil (5 FU), Gemcitabine (Gemzar), methotrexate, Vinorelbine (Navelbine), an EGFR inhibitor such as erlotinib, Trastuzumab (Herceptin, this drug is only of use in women whose breast cancers have the HER-2 gene), Avastin, Platins (cisplatin, carboplatin), Temazolamide, Interferon alpha, and IL-2.

In a particular embodiment, said therapeutic agent is selected from the group consisting of an EGFR inhibitor, an mTOR inhibitor, and a taxane.

In a particular embodiment, the therapeutic procedure is selected from the group consisting of peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, immunohistochemistry staining method, pharmacological study, low-LET cobalt-60 gamma ray therapy, bleomycin, conventional surgery, radiation therapy, high-dose chemotherapy and non-myeloablative allogeneic hematopoietic stem cell transplantation.

In a particular embodiment, the method further comprises obtaining a biological sample from said subject; and analyzing said biological sample with an analytical procedure selected from the group consisting of blood chemistry analysis, chromosomal translocation analysis, needle biopsy, fluorescence in situ hybridization, laboratory biomarker analysis, immunohistochemistry staining method, flow cytometry or a combination thereof. Analysis provides information about progression of the tumor or of the treatment, and is useful for determining dosages to administer, for adjusting dosages during a treatment cycle, and for deciding whether to continue or discontinue the treatments of the invention.

In certain embodiments, the optically active compound used in the methods described herein is enriched with the S-enantiomer shown here, and preferably it is at least 90% S-enantiomer, containing no more than about 10% of the enantiomeric R isomer:

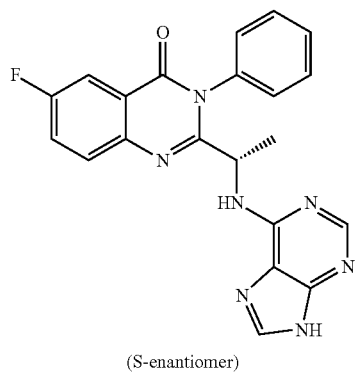 [SMILES: C[C@H](Nc1ncnc2[nH]cnc12)c1nc2ccc(F)cc2c(=O)n1-c1ccccc1]

(S-enantiomer)

In some embodiments, the compound of Formula I used in the methods described herein is at least 80% the S-enantiomer, containing less than 20% of its enantiomeric R-isomer In some embodiments the compound has an enantiomeric excess (e.e.) of at least 90% or at least 95% favoring the S-isomer.

In certain embodiments, the compound is primarily composed of the S-enantiomer, wherein this isomer comprises at least 66-95%, or about 85-99% of the S-isomer, in excess over any R-enantiomer present. In certain embodiments, the compound comprises at least 95% of the S-enantiomer. In the cellular and patient experiments provided in the Example section, the sample of compound I used was over 99% the S enantiomer, with less than 1% of the R enantiomer.

The term "selective PI3Kδ inhibitor" or "selective PI3Kβ inhibitor", etc., as used herein, refers to a compound that inhibits the PI3Kδ or PI3Kβ isozyme, respectively, more effectively than at least one other isozyme of the PI3K family. The selective inhibitor may also inhibit other isozymes of PI3K, but requires higher concentrations to achieve the same degree of inhibition of the other isozymes. "Selective" can also be used to describe a compound that inhibits a particular PI3-kinase more so than a comparable compound. A "selective PI3Kδ inhibitor" compound is understood to be more selective for PI3Kδ than compounds conventionally and generically designated PI3K inhibitors, e.g., wortmannin or LY294002, which are considered non-selective PI3K inhibitors.

"Treating" as used herein refers to inhibiting a disorder, i.e., arresting its development; relieving the disorder, i.e., causing its regression; or ameliorating the disorder, i.e., reducing the severity of at least one of the symptoms associated with the disorder. In some embodiments, "treating" refers to preventing a disorder from occurring in an animal that can be predisposed to the disorder, but has not yet been diagnosed as having it. "Disorder" is intended to encompass medical disorders, diseases, conditions, syndromes, and the like, without limitation.

In certain embodiments, the invention provides methods to treat a solid tumor, typically a non-hematopoietic carcinoma. In some embodiments, the cancer is a solid tumor selected from pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; melanoma; neuroendocrine cancers; CNS cancers; brain tumors; bone cancer; and soft tissue sarcoma. In some embodiments it is lung cancer (non-small cell lung cancer, small-cell lung cancer), colon cancer, CNS cancer, melanoma, ovarian cancer, renal cancer, prostate cancer or breast cancer. In some embodiments, the cancer is breast, lung, colon, renal, ovarian, or prostate cancer.

In certain embodiments, the invention provides methods to treat a solid tumor that is associated with abnormal or undesirable cellular signaling activity mediated by PI3Kβ. In certain embodiments, the solid tumor is selected from the group consisting of pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In one embodiment, the cancer to be treated with the methods described herein is a solid tumor that exhibits a functional loss of PTEN (phosphatase and tensin homolog, a phosphatase that acts as a tumor suppressor) activity. Loss of PTEN activity often occurs in cancers, and enhances the sensitivity of a tumor to PI3K inhibitors. The NCI panel contains a number of cell lines known to have mutations in PTEN, and 70% of those cell lines were inhibited by Compound I, and two of the ones that were not sensitive to Compound I proved to have no functional loss of PTEN activity. The following Table summarizes the cell lines found to be sensitive to Compound I and the known mutations in those cell lines. Of these mutations, only PTEN was found to be significantly correlated with efficacy of Compound I ($p<0.036$).

| Tumor Type | CDKN2 | TP53 | PTEN | PI3KCA | BRAF | HRAS | SMAD4 | BRCA1 |
|---|---|---|---|---|---|---|---|---|
| Hop-92 | X | X | | | | | | |
| KM12 | | X | X | | | | | X |
| SF-268 | X | X | | | | | | |
| SF-295 | | X | X | | | | | |
| SNB-75 | | X | | | | | | |
| UACC-62 | X | | X | | X | | | |
| IGROV-1 | | X | X | | | | X | X |
| OVCAR-3 | | X | | | | | | |
| 786-0 | X | X | X | | | | | |
| A498 | X | | | | | | | |
| CAKI-1 | X | | | | | | | |
| RXF-393 | X | X | X | | | | | |
| TK-10 | | X | | | | | | |
| UO-31 | X | | | | | | | |
| PC-3 | | X | X | | | | | |
| DU-145$_{(RB1)}$ | X | X | | | | | | |
| MCF7 | X | | | E545K | | | | |
| HS-578T | | X | | | | X | | |
| BT-549$_{(RB1)}$ | | X | | | | | | |
| T47D | | X | | H1047R | | | | |
| | 50% | 75% | 35% | 10% | 5% | 5% | 5% | 10% |

Accordingly, solid tumors with significantly reduced PTEN phosphatase activity are particularly suitable for treatment with compound I. The Wellcome Trust Sanger Institute recently published information on the incidence of PTEN mutations in primary tumor tissues, indicating that breast, CNS, cervix, endometrial, kidney, ovary, prostate, skin, testis, and urinary tract tumors frequently include PTEN mutations. Accordingly, in some embodiments, the methods of the invention are used to treat a subject afflicted with one or more of these particular cancers, or a PTEN-deficient cancer selected from breast, CNS, cervix, endometrial, kidney, ovary, prostate, skin, testis, and urinary tract tumors.

In certain embodiments, the method described herein is useful in targeting cells mediating Akt phosphorylation, because compound I inhibits Akt phosphorylation as illustrated in FIG. 4.

For the treatment of a solid tumor, it is advantageous that the compound of Formula I exhibits good activity against p110β, since solid tumors often utilize this isozyme rather than or more than p110δ. Thus in some embodiments, the solid tumor is one that expresses p110β at a higher level than its level of expression of p110δ. In some embodiments, the solid tumor is one with a low level of p110δ activity, such as one expressing less than about 20% as much p110δ as p110β.

In some embodiments, the subject for treatments described herein is one who has been diagnosed with at least one of the cancers described herein as treatable by the use of a compound of Formula I. In some embodiments, the subject has been diagnosed with a cancer named herein, and has proven refractory to treatment with at least one conventional chemotherapeutic agent. Thus in one embodiment, the treatments of the invention are directed to patients who have received one or more than one such treatment and remain in need of more effective treatment.

In one embodiment, the method described herein comprises administering to a subject a compound of formula I described herein, in combination with a therapy used to treat cancer. The "therapy" used to treat cancer, as used herein, is any well-known or experimental form of treatment used to treat cancer that does not include the use of a compound of formula I. In certain embodiments, the combination of a compound of formula I with a conventional or experimental therapy used to treat cancer provides beneficial and/or desirable treatment results superior to results obtained by treatment without the combination. In certain embodiments, said therapies used to treat cancer are well-known to a person having ordinary skill in the art and are described in the literature. Therapies include, but are not limited to, chemotherapy, combinations of chemotherapy, biological therapies, immunotherapy, radioimmunotherapy, and the use of monoclonal antibodies, and vaccines. In certain embodiments, the combination method provides for a compound of formula I administered simultaneously or during the period of administration of the therapy. In certain embodiments, the combination method provides for a compound of formula I administered prior to or after the administration of the therapy. The exact details regarding the administration of the combination may be determined experimentally. The refinement of sequence and timing of administering a compound of formula I with a selected therapy will be tailored to the individual subject, the nature of the condition to be treated in the subject, and generally, the judgment of the attending practitioner.

Additional therapeutic agents for combinations with Compound I include those routinely used in the treatment of solid tumors, particularly Docetaxel, Mitoxantrone, Prednisone, Estramustine, Anthracyclines, (doxorubicin (Adriamycin), epirubicin (Ellence), and liposomal doxorubicin (Doxil)), Taxanes (docetaxel (Taxotere), paclitaxel (Taxol), and protein-bound paclitaxel (Abraxane)), Cyclophosphamide (Cytoxan), Capecitabine (Xeloda) and 5 fluorouracil (5 FU), Gemcitabine (Gemzar), methotrexate, Vinorelbine (Navelbine), an EGFR inhibitor such as erlotinib, Trastuzumab (Herceptin, this drug is only of use in women whose breast cancers have the HER-2 gene), Avastin, Platins (cisplatin, carboplatin), Temazolamide, Interferon alpha, and IL-2.

In certain embodiments, the method comprises administering to said subject, in addition to an effective amount of compound I, at least one therapeutic agent and/or therapeutic procedure selected to treat said cancer in said subject. In certain embodiments, the method comprises administering in addition to a compound of I to said subject, a therapeutically effective amount of an additional therapeutic agent selected from Docetaxel, Mitoxantrone, Prednisone, Estramustine, Anthracyclines, (doxorubicin (Adriamycin), epirubicin (Ellence), and liposomal doxorubicin (Doxil)), Taxanes (docetaxel (Taxotere), paclitaxel (Taxol), and protein-bound paclitaxel (Abraxane)), Cyclophosphamide (Cytoxan), Capecitabine (Xeloda) and 5 fluorouracil (5 FU), Gemcitabine (Gemzar), methotrexate, Vinorelbine (Navelbine), an EGFR inhibitor such as erlotinib, Trastuzumab (Herceptin, this drug is only of use in women whose breast cancers have the HER-2 gene), Avastin, Platins (cisplatin, carboplatin), Temazolamide, Interferon alpha, and IL-2.

The compounds of the invention may be formulated for administration to animal subject using commonly understood formulation techniques well known in the art. Formulations which are suitable for particular modes of administration and for the compounds of formula I may be found in *Remington's Pharmaceutical Sciences*, latest edition, Mack Publishing Company, Easton, Pa.

A compound of the present invention can be administered as the neat chemical, but it is typically preferable to administer the compound in the form of a pharmaceutical composition or formulation. Accordingly, the present invention also provides pharmaceutical compositions that comprise a compound of formula I and a biocompatible pharmaceutical carrier, adjuvant, or vehicle. The composition can include the agent as the only active moiety or in combination with other agents, such as oligo- or polynucleotides, oligo- or polypeptides, drugs, or hormones mixed with excipient(s) or other pharmaceutically acceptable carriers. Carriers and other ingredients can be deemed pharmaceutically acceptable insofar as they are compatible with other ingredients of the formulation and not deleterious to the recipient thereof.

The pharmaceutical compositions are formulated to contain suitable pharmaceutically acceptable carriers, and can optionally comprise excipients and auxiliaries that facilitate processing of the active compounds into preparations that can be used pharmaceutically. The administration modality will generally determine the nature of the carrier. For example, formulations for parenteral administration can comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's solution, Ringer's solution, or physiologically buffered saline. For tissue or cellular administration, penetrants appropriate to the particular barrier to be permeated are used in the formulation. Such penetrants are generally known in the art. For preparations comprising proteins, the formulation can include stabilizing materials, such as polyols (e.g., sucrose) and/or surfactants (e.g., nonionic surfactants), and the like.

Alternatively, formulations for parenteral use can comprise dispersions or suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxy-methylcellulose, sorbitol, or dextran. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT™ series available from Rohm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethlyene sorbitol and sorbitan esters, microcrystalline cellulose, aluminum metahydroxide, bentonite, agar-agar, gum tragacanth, and mixtures thereof.

Liposomes containing the active agent also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See,. e.g., Prescott (Ed.), METHODS IN CELL BIOLOGY, Vol. XIV, p. 33, Academic Press, New York (1976).

The pharmaceutical compositions comprising the agent in dosages suitable for oral administration can be formulated using pharmaceutically acceptable carriers well known in the art. The preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragée cores. Oral formulations can employ liquid carriers similar in type to those described for parenteral use, e.g., buffered aqueous solutions, suspensions, and the like.

Preferred oral formulations include tablets, dragees, and gelatin capsules. These preparations can contain one or excipients, which include, without limitation:
- a) diluents, such as sugars, including lactose, dextrose, sucrose, mannitol, or sorbitol;
- b) binders, such as magnesium aluminum silicate, starch from corn, wheat, rice, potato, etc.;
- c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen;
- d) disintegrating or solubilizing agents such as crosslinked polyvinyl pyrrolidone, starches, agar, alginic acid or a salt thereof, such as sodium alginate, or effervescent compositions;
- e) lubricants, such as silica, talc, stearic acid or its magnesium or calcium salt, and polyethylene glycol;
- f) flavorants and sweeteners;
- g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers.

In some preferred oral formulations, the pharmaceutical composition comprises at least one of the materials from group (a) above, or at least one material from group (b) above, or at least one material from group (c) above, or at least one material from group (d) above, or at least one material from group (e) above. Preferably, the composition comprises at least one material from each of two groups selected from groups (a)-(e) above.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds can be dissolved or suspended in suitable fluids, such as fatty oils, liquid paraffin, or liquid polyethylene glycol with or without stabilizers.

Dragée cores can be provided with suitable coatings such as concentrated sugar solutions, which also can contain gum arabic, talc, polyvinyl pyrrolidone, carbopol gel, polyethylene glycol, and/or titanium dioxide, lacquer solutions, and suitable organic solvents or solvent mixtures.

The pharmaceutical composition can be provided as a salt of the active agent. Salts tend to be more soluble in aqueous or other protonic solvents than the corresponding free acid or base forms. Pharmaceutically acceptable salts are well known in the art. Compounds that contain acidic moieties can form pharmaceutically acceptable salts with suitable cations. Suitable pharmaceutically acceptable cations include, for example, alkali metal (e.g., sodium or potassium) and alkaline earth (e.g., calcium or magnesium) cations.

Compounds of structural formula (I) that contain basic moieties can form pharmaceutically acceptable acid addition salts with suitable acids. For example, Berge, et al., describe pharmaceutically acceptable salts in detail in *J. Pharm. Sci.*, 66:1 (1977). The salts can be prepared in situ during the final isolation and purification of the compounds of the invention or separately by reacting a free base function with a suitable acid.

Representative acid addition salts include, but are not limited to, acetate, adipate, alginate, citrate, aspartate, benzoate, benzenesulfonate, bisulfate, butyrate, camphorate, camphorolsulfonate, digluconate, glycerophosphate, hemisulfate, heptanoate, hexanoate, fumarate, hydrochloride, hydrobromide, hydroiodide, 2-hydroxyethanesulfonate (isothionate), lactate, maleate, methanesulfonate or sulfate, nicotinate, 2-naphthalenesulfonate, oxalate, pamoate, pectinate, persulfate, 3-phenylpropionate, picrate, pivalate, propionate, succinate, tartrate, thiocyanate, phosphate or hydrogen phosphate, glutamate, bicarbonate, p-toluenesulfonate, and undecanoate. Examples of acids that can be employed to form pharmaceutically acceptable acid addition salts include, without limitation, such inorganic acids as hydrochloric acid, hydrobromic acid, sulfuric acid, and phosphoric acid, and such organic acids as oxalic acid, maleic acid, succinic acid, and citric acid.

Basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain alkyl halides such as decyl, lauryl, myristyl, and stearyl chlorides, bromides, and iodides; arylalkyl halides such as benzyl and phenethyl bromides; and others. Products having modified solubility or dispersibility are thereby obtained.

Compositions comprising a compound of the invention formulated in a pharmaceutical acceptable carrier can be prepared, placed in an appropriate container, and labeled for treatment of an indicated condition. Accordingly, there also is contemplated an article of manufacture, such as a container comprising a dosage form of a compound of the invention and a label containing instructions for use of the compound. Kits are also contemplated under the invention. For example, the kit can comprise a dosage form of a pharmaceutical composition and a package insert containing instructions for use of the composition in treatment of a medical condition. In either case, conditions indicated on the label can include treatment of inflammatory disorders, cancer, etc.

Methods of Administration

Pharmaceutical compositions comprising a compound of formula I can be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullarly, intramuscular, intraarticular, intrathecal, and intraventricular injections. Enteral administration modalities include, for example, oral (including buccal and sublingual) and rectal administration. Transepithelial administration modalities include, for example, transmucosal administration and transdermal administration. Transmucosal administration includes, for example, enteral administration as well as nasal, inhalation, and deep lung administration; vaginal administration; and rectal administration. Transdermal administration includes passive or active transdermal or transcutaneous modalities, including, for example, patches and iontophoresis devices, as well as topical application of pastes, salves, or ointments. Parenteral administration also can be accomplished using a high-pressure technique, e.g., POWDERJECT™.

Surgical techniques include implantation of depot (reservoir) compositions, osmotic pumps, and the like. A preferred route of administration for treatment of inflammation can be local or topical delivery for localized disorders such as arthritis, or systemic delivery for distributed disorders, e.g., intravenous delivery for reperfusion injury or for systemic conditions such as septicemia. For other diseases, including those involving the respiratory tract, e.g., chronic obstructive pulmonary disease, asthma, and emphysema, administration can be accomplished by inhalation or deep lung administration of sprays, aerosols, powders, and the like.

The compound of formula I can be administered before, during, or after administration of chemotherapy, radiotherapy, and/or surgery. The formulation and route of administration chosen will be tailored to the individual subject, the nature of the condition to be treated in the subject, and generally, the judgment of the attending practitioner.

The therapeutic index of the compound of formula I can be enhanced by modifying or derivatizing the compounds for targeted delivery to cancer cells expressing a marker that identifies the cells as such. For example, the compounds can be linked to an antibody that recognizes a marker that is selective or specific for cancer cells, so that the compounds are brought into the vicinity of the cells to exert their effects locally, as previously described (see for example, Pietersz, et al., *Immunol. Rev.*, 129:57 (1992); Trail et al., *Science*, 261: 212 (1993); and Rowlinson-Busza, et al., *Curr. Opin. Oncol.*, 4:1142 (1992)). Tumor-directed delivery of these compounds enhances the therapeutic benefit by, inter alia, minimizing potential nonspecific toxicities that can result from radiation treatment or chemotherapy. In another aspect, the compound of formula I and radioisotopes or chemotherapeutic agents can be conjugated to the same anti-tumor antibody.

The characteristics of the agent itself and the formulation of the agent can influence the physical state, stability, rate of in vivo release, and rate of in vivo clearance of the administered agent. Such pharmacokinetic and pharmacodynamic information can be collected through preclinical in vitro and in vivo studies, later confirmed in humans during the course of clinical trials. Thus, for any compound used in the method of the invention, a therapeutically effective dose can be estimated initially from biochemical and/or cell-based assays.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index," which typically is expressed as the ratio LD50/ED50. Compounds that exhibit large therapeutic indices, i.e., the toxic dose is substantially higher than the effective dose, are preferred. The data obtained from such cell culture assays and additional animal studies can be used in formulating a range of dosage for human use. The dosage of such compounds lies preferably within a range of circulating concentrations that include the $ED_{50}$ with little or no toxicity.

For the methods of the invention, any effective administration regimen regulating the timing and sequence of doses can be used. Doses of the agent preferably include pharmaceutical dosage units comprising an effective amount of the agent. As used herein, "effective amount" refers to an amount sufficient to modulate PI3 Kbeta expression or activity and/or derive a measurable change in a physiological parameter of the subject through administration of one or more of the pharmaceutical dosage units. "Effective amount" can also refer to the amount required to ameliorate a disease or disorder in a subject.

Suitable dosage ranges for the compounds of formula I vary according to these considerations, but in general, the compounds are administered in the range of 10.0 µg/kg-15 mg/kg of body weight; 1.0 µg/kg-10 mg/kg of body weight, or 0.5 mg/kg-5 mg/kg of body weight. For a typical 70-kg human subject, thus, the dosage range is from 700 µg-1050 mg; 70 µg-700 mg; or 35 mg-350 mg per dose, and two or more doses may be administered per day. Dosages may be higher when the compounds are administered orally or transdermally as compared to, for example, i.v. administration. In certain embodiments, the treatment of cancers comprises oral administration of up to 750 mg/day of Compound I. The reduced toxicity of this compound permits the therapeutic administration of relatively high doses. For treatment of many solid tumors, a dosage of about 50-100 mg per dose, administered orally once or preferably at least twice per day, is often suitable. In some embodiments, compound I is administered orally, in three to five doses per day, using 20-150 mg per dose for a total daily dose between about 60 and 750 mg. In some embodiments, the total daily dose is between 100 and 500 mg, and in some embodiments the normalized daily dosage (adjusted for subject's body weight) is up to about 60 mg per kg of the treated subject's body weight.

The compounds may be administered as a single bolus dose, a dose over time, as in i.v. or transdermal administration, or in multiple dosages. For IV or transdermal delivery, a dosage may be delivered over a prolonged period of time, and may be selected or adjusted to produce a desired plasma level of the active compound. In some embodiments, the desired level will be at least about 1 micromolar, or at least about 10 micromolar.

When the compound is administered orally, it is preferably administered in two or more doses per day. In some embodiments, three doses per day are administered. In some embodiments four doses per day are administered.

Dosing may be continued for one day or for multiple days, such as about 7 days. In some embodiments, daily dosing is continued for about 14 days or about 28 days. In some embodiments, dosing is continued for about 28 days and is then discontinued for about 7 days; the efficacy of the treatment can be assessed during the break, when treatment with compound I has been stopped, and if the assessment shows that the treatment is achieving a desired effect, another 7-28 day cycle of treatment with Compound I can be initiated.

Depending on the route of administration, a suitable dose can be calculated according to body weight, body surface area, or organ size. The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Subjects that will respond favorably to the method of the invention include medical and veterinary subjects generally, including human patients. Among other subjects for whom the methods of the invention is useful are cats, dogs, large animals, avians such as chickens, and the like. In general, any subject who would benefit from a compound of formula I is appropriate for administration of the invention method.

The biological data disclosed herein was produced using a sample of Compound I that contains less than 1% of the R isomer and >99% $^s$ enantiomer, as determined by chiral HPLC using a 4.6×250 mm Chiralcel OD-H column operated at 40oC, using a flow rate of 1 mL/min of 90:10 hexanes/ethanol. This material was prepared as summarized in FIG. 9. The material was characterized by HPLC to be over 99% pure (according to both 214 nm and 254 nm UV detection), and was also characterized by nmr and electrospray mass spectroscopy. It was a white powder.

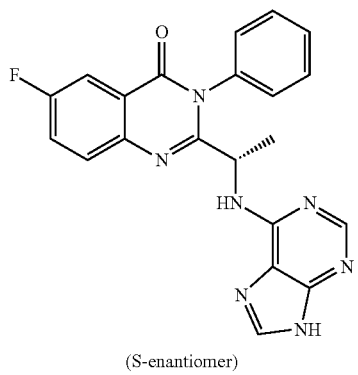 [SMILES: C[C@H](Nc1ncnc2[nH]cnc12)c1nc2ccc(F)cc2c(=O)n1-c1ccccc1]

(S-enantiomer)

The material used in the Examples had the following characteristics:

| Test | Test Result |
| --- | --- |
| Appearance | White powder |
| $^1$H-NMR | Consistent with structure |
| HPLC Assay | 99+% |
| Chiral Purity (HPLC) | 99.2% ee (99.6:0.4 ratio of S:R isomers) |

EXAMPLE 1

Chick Embryo Fibroblast Transformation Assay

Figure 3:
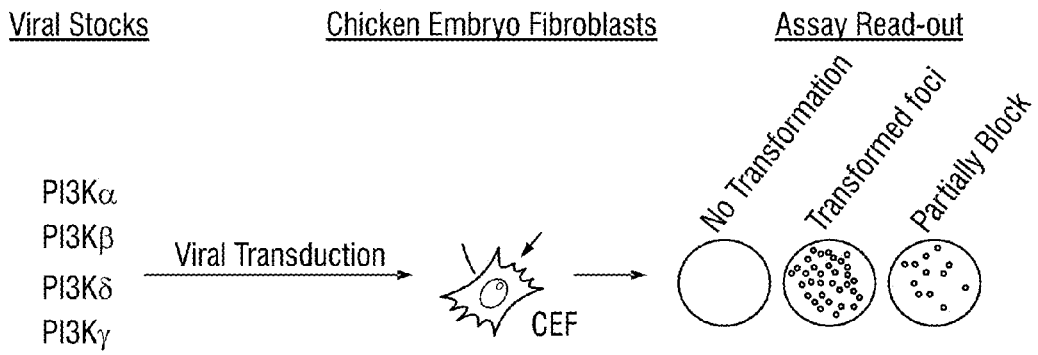
FIG. 3 shows the readout of a functional CEF transformation assay for the relative activity of various isoforms of p110.
Figure 2:
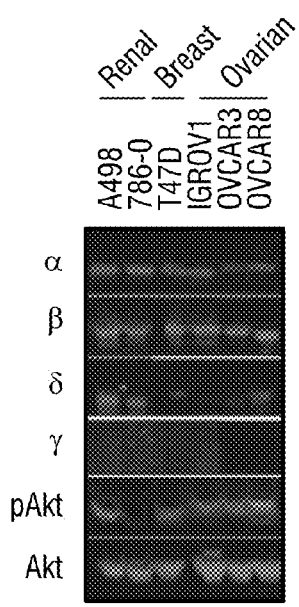
FIG. 2 shows the relative levels of the alpha, beta, delta and gamma isoforms of p110 in six different cancer cell lines, along with levels of Akt and pAkt.

Chick embryo fibroblasts (CEF) are transduced with viral stocks with versions of the human genes for the individual PI3K isoforms p110α, p110β, p110δ and p110γ. These transduced CEF lines are then plated in a growth medium where oncogenically transformed cells form foci that can then be stained and counted. Compound 1 inhibited the formation of transformed foci in CEF cells that had been transduced with p110β with an EC50 of 150 nM. In contrast Compound 1 did not inhibit CEF cells transduced with p110α significantly at the highest concentration tested (2000 nM). Denley A, Kang S, Karst U and Vogt PK, "Oncogenic signaling of class 1 PI3K isoforms." Oncogene (2008) 27: 2561-2574. FIG. 3 illustrates the readout of this assay.

EXAMPLE 2

Preparation of Compound I

Figure 5:
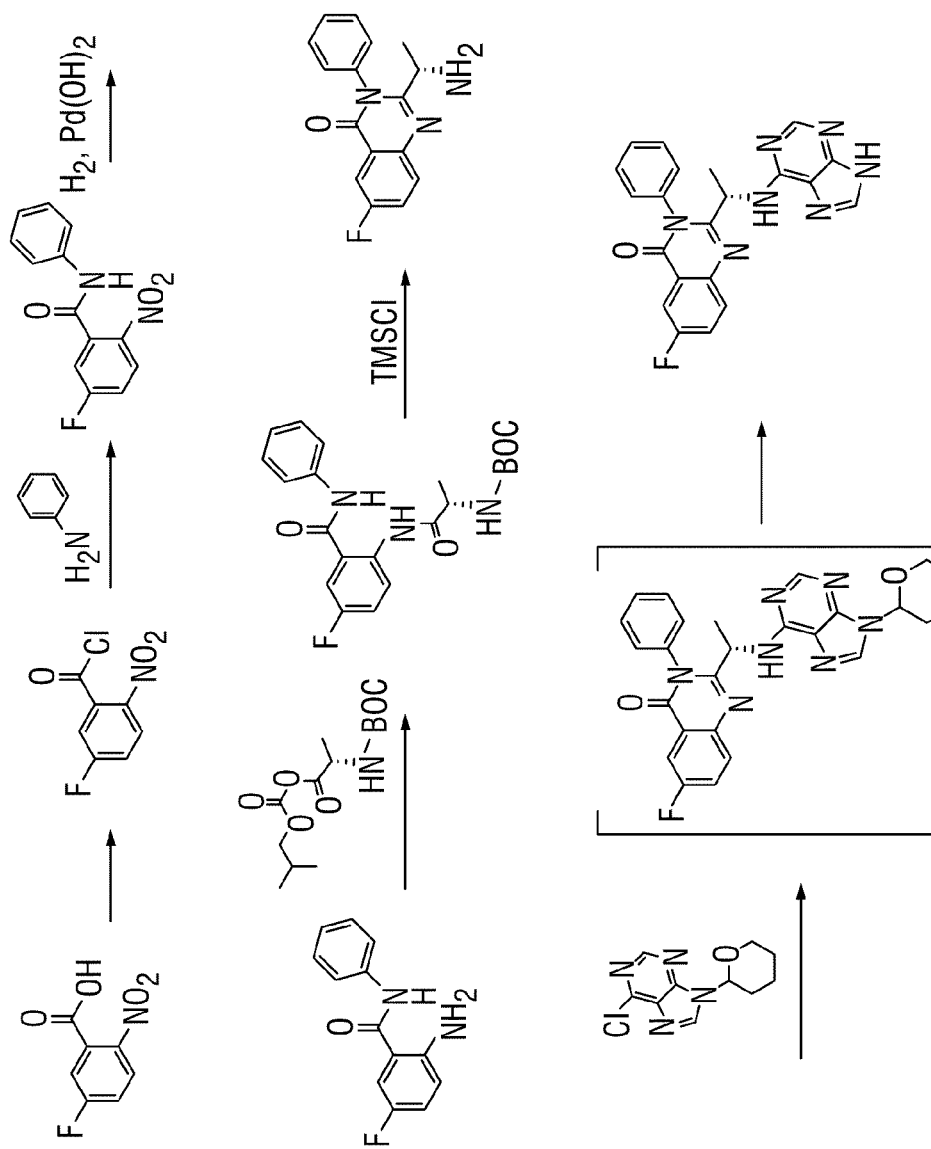
FIG. 5 illustrates a reaction scheme for synthesis of Compound I.

Compound I was synthesized by the route depicted in FIG. 5, using methods known in the art including adaptations of methods described in Zhichkin, et al., Organic Letters, vol. 9(7), 1415-18 (2007), and U.S. Pat. No. 6,800,620.

EXAMPLE 3

Effect of Compound I on Ovarian Cancer Cell Xenografts

Female nu/nu mice bearing OVCAR-3 xenografts (human ovarian cancer cells) were maintained until tumor volume measured about 100 mm$^3$. At that point, treatment began with compound I at a rate of 30 mg/kg administered twice per day. Results of tumor volume measurements over a 36 day period are shown in FIG. 8, and demonstrate that not only was tumor growth inhibited, but the size of the existing tumor was actually reduced by treatment with Compound I.

EXAMPLE 4

Effect of Compound I on Renal Cancer Xenografts

Female nu/nu mice bearing A498 xenografts (human renal cancer cells) were maintained until tumor volume measured about 100 mm$^3$. At that point, treatment began with compound I at a rate of 30 mg/kg administered twice per day. Results of tumor volume measurements over a 20 day period are shown in FIG. 9, which demonstrates that this dosing level provides a significant reduction in tumor growth in vivo.

EXAMPLE 5

Plasma Levels of Compound I in Mice Carrying Tumor Xenografts

Plasma levels of Compound I were observed in female nu/nu mice carrying one of the cancer cell xenografts used in the preceding two examples. Compound I was administered in a single dose at a rate of 30 mg/kg to each test subject, and plasma levels were monitored for 12 hours thereafter. Plasma levels of Compound I peaked around 2-4 hours after administration in each case, and had essentially returned to zero 8 hours after the single dose at this rate, as shown in FIG. 10. The peak plasma concentration for these subjects, after a single injection at the dose shown to be effective for inhibiting tumor growth of each xenograft (see the preceding examples, and FIGS. 8-9) were generally below about 7000 ng/mL.

EXAMPLE 6

Pharmacokinetics and Toxicokinetics of Compound I in Rats

Compound I was dosed at 60, 120, or 240 mg/kg/day administered as a single dose for up to 14 days in healthy rats. FIG. 11 shows the measured blood levels of Compound I over a 24-hour period for each test subject during the first day of treatment (dashed lines) and the last day of treatment (solid lines) for the tolerated doses. The peak concentration of compound I (Cmax) and area under the curve (AUC) for tolerated doses were higher than those observed with effective doses of Compound I in the xenograft model tumors in mice. For example, the 60 mg/kg per day dosing produced a Cmax of 7300 ng/mL, while the C max for effective antitumor doses in the xenograft test were 2800 and 5600 ng/mL. Similarly, the AUC for the 60 mg/kg/day dosing in this study was 58,000 ng-h/mL, while the corresponding AUC in the xenograft bearing mice receiving effective treatment doses were 15,000 and 18,000 ng-h/mL.

The invention claimed is:

1. A method of treating a solid tumor in a subject comprising administering to said subject an optically active compound of formula I

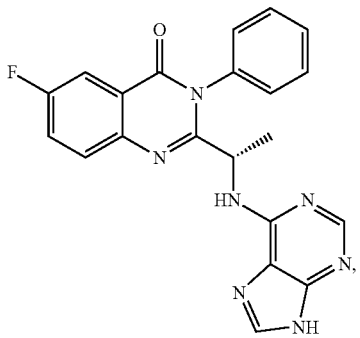

or a pharmaceutically acceptable salt thereof,
or a pharmaceutical composition comprising an optically active compound of formula I or a pharmaceutically acceptable salt thereof;
wherein the amount of the optically active compound of formula I or a pharmaceutically acceptable salt thereof is an amount effective to treat the solid tumor.

2. The method of claim 1, wherein the solid tumor is selected from the group consisting of pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors, bone cancer, and soft tissue sarcoma.

3. The method of claim 1, wherein the solid tumor is selected from non-small cell lung cancer, small-cell lung cancer, colon cancer, CNS cancer, melanoma, ovarian cancer, renal cancer, prostate cancer and breast cancer.

4. The method of claim 1, wherein the pharmaceutical composition comprises the optically active compound of formula I and the corresponding R-enantiomer of the optically active compound of formula I, or pharmaceutically acceptable salts thereof, and wherein the optically active compound of formula I or pharmaceutically acceptable salt thereof predominates over the corresponding R-enantiomer of the optically active compound of formula I or pharmaceutically acceptable salt thereof by a ratio of at least about 9:1.

5. The method of claim 1, wherein the pharmaceutical composition comprises the optically active compound of formula I and the corresponding R-enantiomer of the optically active compound of formula I, or pharmaceutically acceptable salts thereof, and wherein the optically active compound of formula I or pharmaceutically acceptable salt thereof predominates over the corresponding R-enantiomer of the optically active compound of formula I or pharmaceutically acceptable salt thereof by a ratio of at least about 19:1.

6. The method of claim 1, wherein the optically active compound, or pharmaceutically acceptable salt thereof, or pharmaceutical composition is administered orally.

7. The method of claim 1, wherein the optically active compound of formula I, or pharmaceutically acceptable salt thereof, or pharmaceutical composition is administered in solid form.

8. The method of claim 7, wherein the solid form comprises the optically active compound of formula I or pharmaceutically acceptable salt thereof admixed with at least one pharmaceutically acceptable excipient.

9. The method of claim 7, wherein the solid tumor is ovarian, renal, breast, lung, colon or prostate cancer.

10. The method of claim 1, wherein the subject is refractory to chemotherapy treatment, or in relapse after treatment with chemotherapy.

11. The method of claim 1, wherein the optically active compound of formula I or pharmaceutically acceptable salt thereof is administered at a dose of 20-500 mg/day.

12. The method of claim 1, wherein the optically active compound of formula I or pharmaceutically acceptable salt thereof is administered at a dose of 50-250 mg/day.

13. The method of claim 1, wherein the optically active compound of formula I or pharmaceutically acceptable salt thereof is administered at a dose of 50-150 mg twice per day.

14. The method of claim 1, wherein the optically active compound of formula I or pharmaceutically acceptable salt thereof is administered at least twice daily.

15. The method of claim 1, wherein the subject is a human subject.

16. The method of claim 15, wherein the concentration of the optically active compound of formula I or pharmaceutically acceptable salt thereof in the subject's blood is between 40-3000 ng/mL over a 12 hour period from the time of administration.

17. The method of claim 15, wherein the concentration of the optically active compound or pharmaceutically acceptable salt thereof in the subject's blood is between about 100 nM and 2000 nM.

18. The method of claim 1, wherein the optically active compound of formula I, or pharmaceutically acceptable salt thereof, or pharmaceutical composition is administered to the subject orally, intravenously or by inhalation.

19. The method of claim 1, further comprising administering in addition to the optically active compound of formula I or pharmaceutically acceptable salt thereof to said subject, a therapeutically effective amount of at least one therapeutic agent and/or therapeutic procedure to treat said solid tumor in said subject.

20. The method of claim 19, wherein said therapeutic agent is selected from the group consisting of an EGFR inhibitor, an mTOR inhibitor, a platin, and a taxane.

21. The method of claim 19, wherein said therapeutic procedure is selected from the group consisting of peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, immunohistochemistry staining method, pharmacological study, low-LET cobalt-60 gamma ray therapy, bleomycin, conventional surgery, radiation therapy, high-dose chemotherapy and non-myeloablative allogeneic hematopoietic stem cell transplantation.

22. The method of claim 1 further comprising obtaining a biological sample from said subject; and analyzing said biological sample with an analytical procedure selected from the group consisting of blood chemistry analysis, chromosomal translocation analysis, needle biopsy, fluorescence in situ hybridization, laboratory biomarker analysis, immunohistochemistry staining method, flow cytometry or a combination thereof.

23. The method of claim 22, wherein the optically active compound of formula I, or pharmaceutically acceptable salt thereof, or pharmaceutical composition is administered twice daily for about 28 days, and is then discontinued for at least 7 days.

24. The method of claim 19, wherein said therapeutic agent is selected from the following group consisting of docetaxel, mitoxantrone, prednisone, estramustine, anthracyclines, taxanes, cyclophosphamide, capecitabine, 5-fluorouracil, gemcitabine, methotrexate, vinorelbine, an EGFR inhibitor, trastuzumab, bevacizumab, platins, temazolamide, interferon alpha, and IL-2.

25. The method of claim 19, wherein said therapeutic agent is selected from the following group consisting of docetaxel, mitoxantrone, prednisone, estramustine, doxorubicin, epirubicin, liposomal doxorubicin, paclitaxel, and protein-bound paclitaxel, cyclophosphamide, capecitabine, 5-fluorouracil, gemcitabine, methotrexate, vinorelbine, erlotinib, trastuzumab, bevacizumab, cisplatin, carboplatin, temazolamide, interferon alpha, and IL-2.

* * * * *